United States Patent
Curley, Jr. et al.

(10) Patent No.: US 6,696,606 B2
(45) Date of Patent: Feb. 24, 2004

(54) SOLID PHASE SYNTHESIS OF ARYLRETINAMIDES

(75) Inventors: Robert W. Curley, Jr., Columbus, OH (US); Serena M. Mershon, St. Louis, MO (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 10/191,786

(22) Filed: Jul. 8, 2002

(65) Prior Publication Data

US 2003/0105164 A1 Jun. 5, 2003

Related U.S. Application Data (60) Provisional application No. 60/303,616, filed on Jul. 6, 2001.

(51) Int. Cl.[7] ............... C07C 237/20; C07C 233/64; C07C 231/02; A61K 31/195; A61K 31/16
(52) U.S. Cl. ............... 564/142; 564/155; 564/158; 564/182; 554/104; 554/105; 554/106; 554/107; 554/108; 554/109; 554/110; 554/111; 554/112; 554/114; 560/104; 562/430; 562/453; 562/457
(58) Field of Search ............... 554/104, 105, 554/106, 107, 108, 109, 110, 111, 112, 114; 560/104; 562/430, 453, 457; 564/142, 155, 158, 182

(56) References Cited

U.S. PATENT DOCUMENTS

| | | | |
|---|---|---|---|
| 4,108,880 A | | 8/1978 | Gander et al. ............ 260/410.5 |
| 4,190,594 A | | 2/1980 | Gander et al. ............... 260/404 |
| 5,399,757 A | * | 3/1995 | Maryanoff ................... 564/133 |
| 5,731,320 A | * | 3/1998 | Wagner et al. ............... 514/291 |
| 6,117,845 A | | 9/2000 | Clagett-Dame et al. ...... 514/435 |

OTHER PUBLICATIONS

Abstract, Publ. No. JP 4–54119A, "5–Lipoxygenase Inhibitor" by Hirozumi, et al., Feb. 1992, col. 2, p. 127, cols. 1 and 2, p. 131.

Abstract, "Solid–phase assisted synthesis of a library of N–(4–hydroxyphenyl)retinamide (4–HPR) analogs" By Mershon, et al., Aug. 2001 American Chemical Society Meeting.

Abstract, "Solid Phase–Assisted Synthesis and Screening of a Library of N–(4–Hydroxyphenyl)Retinamide Analogs" by Mershon, et al., Jun. 2002 FASEB Summer Research Conference.

Abstract, "Photo/affinity label analogs of N–(4–hydroxyphenyl)retinamide" by Barnett, et al., Aug. 2002 American CHemical Society Meeting.

* cited by examiner

*Primary Examiner*—Peter O'Sullivan
(74) *Attorney, Agent, or Firm*—Calfee, Halter & Griswold, LLP (57) ABSTRACT

A solid phase synthetic method for preparing arylretinamides is provided. The method comprises reacting hexachloroacetone with a solvent-suspended resin-bound triphenylphosphine to provide a suspension comprising an activated chlorinating reagent; reacting retinoic acid with the activated chlorinating reagent to provide retinoyl chloride; adding pyridine and a select arylamine to the resulting mixture; and stirring the resulting mixture for a time and at a temperature sufficient for the select arylamine to react with the retinoyl chloride and provide the arylretinamide. Also provided, are select arylretinamides that can be prepared by the present method, and methods of using such arylretinamides to induce apoptosis in cancer cells.

4 Claims, 2 Drawing Sheets

Figure 1. Retinoic Acid

Figure 2. *N*-(4-Hydroxyphenyl)retinamide (4-HPR)

Figure 3. Synthetic Scheme

Figure 4.

SOLID PHASE SYNTHESIS OF ARYLRETINAMIDES

This application claims priority from U.S. Provisional Application Serial No. 60/303,616 filed on Jul. 6, 2001, which is incorporated herein in its entirety.

This work was supported, at least in part, by grant CA 49837 from the National Institutes of Health. The government has certain rights in this invention.

FIELD OF THE INVENTION

The present invention relates to compounds, particularly arylretinamides, for treating or preventing cancer in a mammalian subject and methods of making such arylretinamides.

BACKGROUND

Breast cancer kills thousands of women annually. While surgical intervention has saved the lives of many women, radical and partial mastectomies often prove physically and emotionally debilitating. Moreover, patients who have undergone surgery and subsequent chemotherapy often experience recurrence.

Drugs for preventing or treating breast cancer, as well as other cancers, are desirable, and many research efforts have focused on the development of such drugs. One such drug is retinoic acid, a metabolite of vitamin A. Retinoic acid and certain amide analogs of this compound display cancer preventive activity and, thus, have been proposed as cancer chemopreventive agents (Moon et al. Cancer Res. (1979) 39, 1339–1346). Similarly, other retinoic acid analogs such as retinyl acetate, 13-cis-retinoic acid, and glucuronide analogs of retinoic acid also display cancer preventive activity, including breast cancer preventative activity (Hill, D. L. et al. Ann. Rev. Nutrition (1992) 12, 161–181 and Mehta, R. G. et al. Oncology (1991) 48, 1505–1509).

Unfortunately, retinoic acid and most of its closely related analogs exhibit relatively high toxicity, thus impeding their use in humans (Biesalski, H. K. Toxicology (1989) 57, 117–161). Use of most of these compounds results in side effects such as teratogenicity, hepatotoxicity, scaly skin, hair loss and headaches. Accordingly, researchers have continued to pursue the synthesis of retinoic acid analogs with increased potency and/or reduced toxicity for application as cancer preventative agents.

It has also been found that N-(4-hydroxyphenyl) retinamide (hereinafter "4-HPR"), an analog of retinoic acid, displays chemopreventive activity in breast cancer (Moon et al. Cancer Res. (1979) 39, 1339–1346). Indeed, 4-HPR, when combined with calcium glucarate, synergistically exerts an increased breast cancer chemopreventive activity in carcinogen-induced rat mammary tumors (Abou-Issa, H. M. et al.(1988) Proc. Natl. Acad. Sci. USA 85, 4181–4184). However, 4-HPR still displays teratogenic potential as evidenced by studies in the rat, mouse and the rabbit. (See Kenel, M. F., Krayer, J. H., Merz, E. A. and Pritchard, J. R. (1988) "Teratogenicity of N-(4-hydroxyphenyl)-all-trans retinamide in rats and rabbits." Teratogenesis, Carcinogenesis and Mutagenesis 8:1–11; Kochhar, D. M. Shealy, Y. F., Penner, J. D. and Jiang, H. (1992) "Retinamides: hydrolytic conversion of retinoylglycine to retinoic acid in pregnant mice contributes to teratogenicity." Teratology 45:175–185.) Furthermore, 4-HPR impairs night vision in human patients (Kaiser-Kupfer, M. I., Peck, G. K., Caruso, R. C., Jaffe, J D., DiGiovanna, J. J., Gross, E. G. (1986) "Abnormal retinal function associated with fenretinide, a synthetic retinoid." Arch Ophthalmol.104:69–70.; Costa, A., Malone, W., Perloff, M., Buranelli, F., Campa, T., Dossena, G., Magni, A., Pizzichetta, M., Andreoli, C., DelVecchio, M., Formelli, F., and Barbier, A. (1989) "Tolerability of the synthetic retinoid Fenretinide (HPR)." Eur. J. Cancer Clin. Oncol. 25:805–808).

Thus, there still remains a long-felt need to have stable chemopreventive drugs for the prevention and treatment of various cancers, including breast cancer.

SUMMARY OF THE INVENTION

In one aspect, the present invention provides compounds for treating or preventing cancer, particularly breast cancer in a subject. The compounds are new arylretinamides and pharmaceutical compositions that contain one of more of the present arylretinamides. The arylretinamides have structure A, B, or C below:

Structure A wherein $R_2$ is H, OH, $NO_2$, $CH_2OH$, a halide, or an alkyl comprising 1–4 carbon atoms, $R_3$ is H, OH, $NO_2$, $CO_2CH_3$, $CO_2CH_2CH_3$, $CO_2(CH_2)_2CH_3$, $CO_2(CH_2)_3CH_3$, $CO_2H$, $CH_2OH$, a halide, or an alkyl comprising 1–4 carbon atoms;

$R_4$ is H, OH, $OCH_3$, $OCH_2CH_3$, $O(CH_2)_2CH_3$, $O(CH_2)_3CH_3$, $SO_2CH_3$, $SO_2CH_2CH_3$, $SO_2(CH_2)_2CH_3$, $SO_2(CH_2)_3CH_3$, $NH_2$, $NHCOCH_3$, $NHCOCH_2CH_3$, $NHCO(CH_2)_2CH_3$, $NHCO(CH_2)_3CH_3$, $NHCOCF_3$, $N_3$, NCS, a halide, an alkyl comprising 1–4 carbon atoms, or $NHCOCH_2X$, wherein X is a halide;

$R_5$ is H, $NO_2$, $C(CH_3)_3$, $C(CH_2CH_3)_3$, $C((CH_2)_2CH_3)_3$, $C((CH_2)_3CH_3)_3$, $CO_2CH_3$, $CO_2CH_2CH_3$, $CO_2(CH_2)_2CH_3$, $CO_2(CH_2)_3CH_3$, a halide, or an alkyl comprising 1–4 carbon atoms, and $R_6$ is H, $CO_2H$, $CO_2CH_3$, $CO_2CH_2CH_3$, $CO_2(CH_2)_2CH_3$, $CO_2(CH_2)_3CH_3$, a halide or an alkyl comprising 1–4 carbon atoms;

provided however that when $R_2$, $R_3$, $R_4$, $R_5$, and $R_6$ are all H, $R_4$ is not OH or $OCH_2CH_3$; and also provided that when $R_3$, $R_5$, and $R_6$ are all H, and $R_2$ is OH, $R_4$ is not $CO_2CH_3$.

Structure B wherein the OH group is at position 2, 4, or 5 when the retinamido group is at linked to position 1, and the OH group is at position 3 when the rentinamido group is linked to position 2.

Structure C wherein $R_7$ is $C_1$ to $C_4$ alkyl.

The present arylretinamides find use in the treatment of cancer in a mammalian subject, including a human subject. Use for treating a particular cancer is initially shown employing an apoptosis assay in a cancer cell line that serves as an experimental model for the particular cancer. Examples of such cell lines include the human breast cancer cell line MCF7 and the human neuroblastoma cell line LA1-15n.

In another aspect the present invention provides methods of treating cancer in a mammalian subject. The present methods comprise administering a biologically effective amount of one or more of present arylretinamides to a mammalian subject, particularly a human subject, who is at risk of or has been diagnosed as having cancer.

In another aspect, the present invention provides a method for synthesizing arylretinamides. The method is a solid phase synthetic scheme and comprises reacting hexachloroacetone with a solvent-suspended resin-bound triphenylphosphine to provide a suspension comprising an activated chlorinating reagent; reacting retinoic acid with the activated chlorinating reagent to provide retinoyl chloride; adding pyridine and a select arylamine to the resulting mixture; and stirring the resulting mixture for a time and at a temperature sufficient for the select arylamine to react with the retinoyl chloride and provide the arylretinamide. Preferably, the method further comprises the step of purifying the arylretinamide from the suspension.

DETAILED DESCRIPTION OF THE INVENTION

Definitions:

Herein, "apoptosis" is used in a broad sense and refers to the orderly or controlled form of cell death that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis, all of which are known in the art. In particular, apoptosis can be measured using the assays described below and in the Examples.

"Cancer cell" or "cancerous cell" means a cell in or from a carcinoma, lymphoma, sarcoma or leukemia.

"Tumor" refers to a spontaneous, new growth of tissue in the body that forms an abnormal mass. Tumors are comprised of cells and such cells are known as tumor cells.

Tumors and cells derived from tumors can be either benign or malignant. Cells that are malignant have a variety of properties that benign cells and non-tumor cells do not have. Malignant cells invade, grow and destroy adjacent tissue, metastasize, and usually grow more rapidly than benign tumor cells. "Neoplasm" is essentially synonymous with tumor.

As used herein, the term "subject" refers to a mammalian animal, preferably a human.

By "treating" is meant curing, ameliorating or tempering the severity of the cancer or the symptoms associated therewith. "Preventing" means preventing the occurrence of the cancer, or tempering the severity of the cancer if it is develops subsequent to the administration of the instant compositions. The terms "treating," "treatment," and "therapy" as used herein refer to curative therapy, prophylactic therapy, and preventative therapy.

Synthetic Methods

In one aspect the present invention provides a solid phase method of synthesizing arylretinamides. Such method comprises reacting hexachloroacetone with a solvent-suspended resin-bound triphenylphosphine to provide a suspension comprising an activated chlorinating reagent. Retinoic acid is added to the resulting suspension at a suitable temperature (e.g., −78 to 25° C.) and reacted with the activated chlorinating reagent to provide retinoyl chloride. Thereafter, pyridine and a select arylamine (i.e., an arylamine with the appropriate aryl group and side chains for producing the desired arylretinamide) are added to the resulting mixture, which is then stirred for a time and at a temperature sufficient for the select arylamine to react with the retinoyl chloride and provide the desired arylretinamide. Preferably, the method further comprises the step of purifying the arylretinamide from the suspension Purification, preferably, is accomplished by treatment with solid phase reagents to remove unreacted starting materials followed by chromatography.

Figure 1:
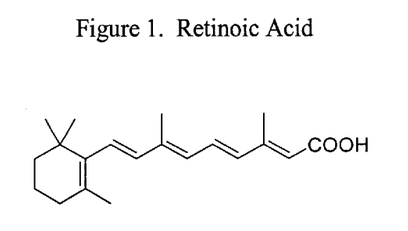
FIG. 1 shows the structure of retinoic acid.
Figure 2:
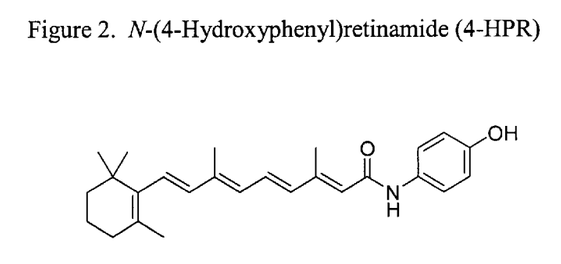
FIG. 2 shows the structure of 4-HPR.
Figure 3:
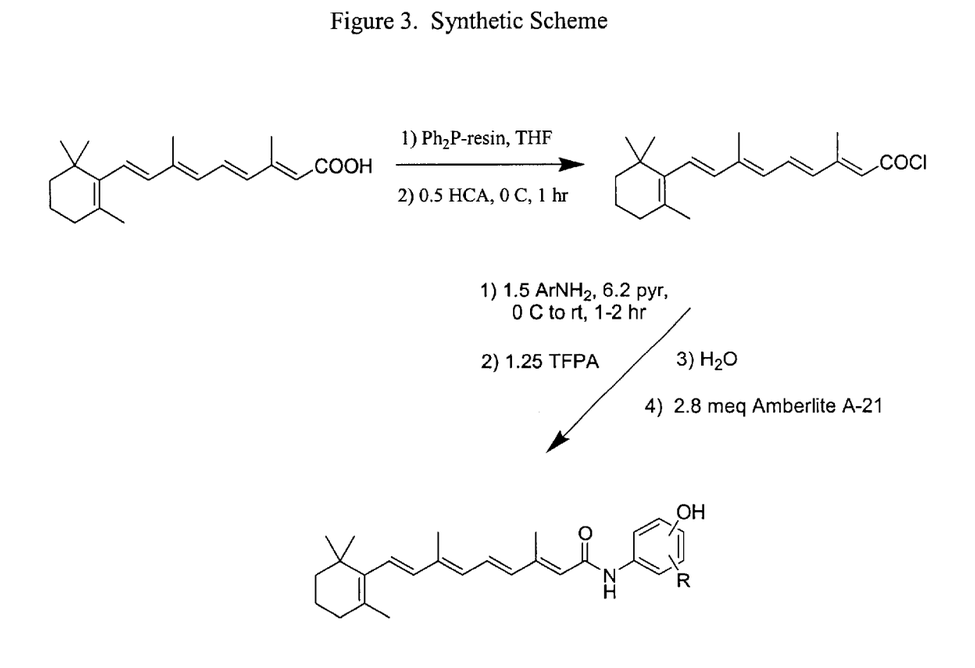
FIG. 3 is a schematic representation of a method of synthesizing arylretinamides.

In one embodiment, which is schematically represented in FIG. 3, the method comprises suspending 3.0 equivalents of resin-bound triphenylphosphine in tetrahydrofuran with 1 equivalent of retinoic acid. To this is added 0.5 equivalents of hexachloroacetone (HCA) at 0° C. to form a reactive chlorinating reagent which generates retinoyl chloride (3). After 60 minutes, 1.5 equivalents of a suitable aminophenol (4) and pyridine (6.2 equivalents) are added and the mixture stirred at 25° C. for 60 minutes. After filtration and resuspension in tetrahydrofuran, to the mixture is then added tetrafluorophthalic anhydride to trap unreacted aminophenol. The resulting acid, along with unreacted retinoic acid, is bound to a tertiary amine ion-exchange resin, solids removed by filtration, and the resulting arylretinamide purified by silica gel chromatography (ethyl acetate/hexane or ether/hexane). Examples of arylretinamides that can be synthesized by the present method include, but are not limited to, the arylretinamides 1–50 depicted in Tables 1 and 2.

Arylretinamides

In another aspect, the present invention provides arylretinamides that induce apopotosis of one or more types of cancer cells, for example mammary cancer cells and prostate cancer cells. The present arylretinamides have Structures A, B, or C below:

Structure A wherein
- R₂ is H, OH, NO₂, CH₂OH, a halide, or an alkyl comprising 1–4 carbon atoms, R₃ is H, OH, NO₂, CO₂CH₃, CO₂CH₂CH₃, CO₂(CH₂)₂CH₃, CO₂(CH₂)₃CH₃, CO₂H, CH₂OH, a halide, or an alkyl comprising 1–4 carbon atoms;
- R₄ is H, OH, OCH₃, OCH₂CH₃, O(CH₂)₂CH₃, O(CH₂)₃CH₃, SO₂CH₃, SO₂CH₂CH₃, SO₂(CH₂)₂CH₃, SO₂(CH₂)₃CH₃, NH₂, NHCOCH₃, NHCOCH₂CH₃, NHCO(CH₂)₂CH₃, NHCO(CH₂)₃CH₃, NHCOCF₃, N₃, NCS, a halide, an alkyl comprising 1–4 carbon atoms, or NHCOCH₂X, wherein X is a halide;
- R₅ is H, NO₂, C(CH₃)₃, C(CH₂CH₃)₃, C((CH₂)₂CH₃)₃, C((CH₂)₃CH₃)₃, CO₂CH₃, CO₂CH₂CH₃, CO₂(CH₂)₂CH₃, CO₂(CH₂)₃CH₃, a halide, or an alkyl comprising 1–4 carbon atoms, and
- R₆ is H, CO₂H, CO₂CH₃, CO₂CH₂CH₃, CO₂(CH₂)₂CH₃, CO₂(CH₂)₃CH₃, a halide or an alkyl comprising 1–4 carbon atoms;

provided however that when R₂, R₃, R₄, R₅, and R₆ are all H, R₄ is not OH or OCH₂CH₃; and also provided that when R₃, R₅, and R₆ are all H, and R₂ is OH, R₄ is not CO₂CH₃.

Structure B wherein the OH group is at position 2, 4, or 5 when the retinamido group is at linked to position 1, and the OH group is at position 3 when the rentinamido group is linked to position 2.

Structure C wherein R₇ is C₁ to C₄ alkyl.

In one aspect, the present compounds are halo, preferably bromo or chloro, hydroxyphenyl retinamides. Optionally, the compounds in this embodiment further comprise an alkyl group, preferably an alkyl group comprising from 1 to 4 carbon atoms, more preferably a methyl group, which is attached to the phenyl moiety. Examples of compounds in this group are compounds 10–15 as shown in Table 1 below.

In another aspect, the present compounds are hydroxy-alkylphenyl retinamides or hydroxy-alkoxyphenyl retinamides. Preferably, the alkyl groups attached to the phenyl moiety comprise from 1 to 4 carbon atoms. More preferably, the compounds are hydroxy-methylphenyl or hydroxy-methoxyphenyl retinamides. Examples of compounds in this group are compounds 9, 31, and 32 as shown in Table 1 below.

In another aspect, the compounds are hydroxy-nitrophenyl retinamides or alkylsulfonyl-hydroxy retinamides. Preferably the alkyl sulfonyl group comprises from 1 to 4 carbon atoms. More preferably the compound in this class is an ethylsulfonyl-hydroxy, retinamides. Examples of compounds in this group are 16–19, and 30 as shown in Table 1 below.

In another aspect, the present compounds are hydroxy-napthylphenyl retinamides. Examples of compounds in this group are compounds 47–50 as shown in Table 2 below.

In another aspect, the present compounds are N-alkyl (hydroxyphenyl) retinamides. Preferably the alkyl group which is attached to the N comprises from 1 to 4 carbon atoms. An example of a compound in this group is compound 46 as shown in Table 2 below.

In another aspect, the present compounds are aminophenyl retinamides. An example of a compound in this group is compound 33 as shown in Table 1 below.

In another aspect, the compounds are alkylhydroxyphenyl retinamides. Preferably, the compounds in this group are hydroxymethylphenyl retinamides. Examples of compounds in this group are compounds 1–8 as shown in Table 1 below.

In another aspect, the compounds are carboxy-hydroxyphenyl retinamides selected from the group consisting of 20–29 as shown in Table 1 below.

The present compounds do not include the arylretinamides 41–45 as shown in Table 1 below.

The present arylretinamides are used to induce apopotosis in one or more types of cancer cells and to prevent or treat related cancers in a mammal subject, including a human subject. The efficacy of the present arylretinamides in preventing or treating a particular cancer is initially determined by contacting cells that serve as an in vitro model of the particular cancer with the arylretinamide and evaluating the ability of the arylretinamide to induce apopoptosis in the model cells. Such assays include, but are not limited to, the Comet assay, the TUNEL assay, apoptosis assays using annexin V conjugates, and apoptosis assays that are based on protease activity in the cell.

Comet (Single-Cell Gel Electrophoresis) Assay to Detect Damaged DNA

The Comet assay, or single-cell gel electrophoresis assay, is used for rapid detection and quantitation of DNA damage from single cells. The Comet assay is based on the alkaline lysis of labile DNA at sites of damage. Cells are immobilized in a thin agarose matrix on slides and gently lysed. When subjected to electrophoresis, the unwound, relaxed DNA migrates out of the cells. After staining with a nucleic acid stain, cells that have accumulated DNA damage appear as bright fluorescent comets, with tails of DNA fragmentation or unwinding. In contrast, cells with normal, undamaged DNA appear as round dots, because their intact DNA does not migrate out of the cell.

TUNEL Assay

When DNA strands are cleaved or nicked by nucleases, a large number of 3'-hydroxyl ends are exposed. In the TUNEL assay (terminal deoxynucleotidyl transferase dUTP nick end labeling), these ends are labeled with UTP using mammalian terminal deoxynucleotidyl transferase (TdT), which covalently adds labeled nucleotides to the 3'-hydroxyl ends of these DNA fragments in a template-independent fashion. The UTP is then detected using specific probes (e.g., you can incorporate BrdUTP and then use a fluorescent anti-BrdU antibody). The assay can be used on cells in situ or the cells can be analyzed by flow cytometry.

Apoptosis Assays Using Annexin V Conjugates

The human anticoagulant annexin V is a 35–36 kilodalton, $Ca^{2+}$-dependent phospholipid-binding protein that has a high affinity for phosphatidylserine (PS). In normal viable cells, PS is located on the cytoplasmic surface of the cell membrane. However, in apoptotic cells, PS is translocated from the inner to the outer leaflet of the plasma membrane, where it is associated with lipid "rafts"—regions of the plasma membrane that are insoluble in detergents, high in cholesterol and sphingolipids, that sequester glycosylphosphatidylinositol (GPI)-linked proteins and tyrosine-phosphorylated proteins and that seem to be involved in signal transduction. Annexin V that is conjugated to various detectable molecules (i.e., fluorescent molcules) are reacted with cells thought to be undergoing apoptosis. If PS is located on the outer surface of the plasma membrane, the annexin V conjugate will bind and be detectable.

Apoptosis Assays Based on Protease Activity

Members of the caspase (CED-3/ICE) family of proteases are crucial mediators of the complex biochemical events associated with apoptosis. In particular, caspase-3 (CPP32/apopain), which has a substrate specificity for the amino acid sequence Asp-Glu-Val-Asp (DEVD), cleaves a number of different proteins, including poly(ADP-ribose) polymerase (PARP), DNA-dependent protein kinase, protein kinase, and actin. Procaspase-3 is released from the mitochondria into the cytoplasm during apoptosis and activated to caspase-3 by an as-yet-unknown enzyme. Assays for caspase comprise addition of substrates for the enzyme that, for example, increase their fluorescence upon cleavage by caspase 3.

Arylretinamides with Reduced Side Effects

Preferably, the arylretinamide does not compete with all-trans-[$^3$H]-RA for binding to retinoic acid receptors (RARs) and with [$^3$H]-9-cis RA for binding to RXR-y. The ability of the present arylretinamide to compete with all-trans-[$^3$H]-RA for binding to RARs and with [$^3$H]-9-cis RA for binding to RXR-y is determined using an in vitro ligand binding assay as described previously in Clagett-Dame M., and Repa, J. J. (1997) Methods Enzymol 282:13–24, which is specifically incorporated herein by reference. Briefly, recombinant human RARα is expressed as a fusion in protein E. coli (Clagett-Dame M., and Repa, J. J. (1997) Methods Enzymol 282:13–24; Repa, J. J. et al. (1997) Proc. Natl. Acad. Sci. 90: 7293–7297). Human RARγ, mouse RARβ, and mouse RXRγ are present in nuclear extracts prepared from insect cells infected with baculovirus expression vectors (Clagett-Dame M., and Repa, J. J. (1997) Methods Enzymol 282:13–24). [$^3$H]-all-trans-RA (72 Ci/mmole) or [$^3$H]-9-cis RA (74.5 Ci/mmole) is added to receptor containing extracts (RAR, 5 nM, and RXR, 10 nM, respectively) in the presence or absence of increasing concentrations of unlabeled ligand (at-RA, 4HPR or the present arylretinamide) and incubated at 4° C. for 3 hr. The hydroxylapatite (HAP) assay is used to separate ligand bound to receptor from that free in solution (Clagett-Dame M., and Repa, J. J. (1997) Methods Enzymol 282:13–24; Repa J. J., Prot Express Purif. (1993) 9:319–330). A liquid scintillation counter is used to measure the amount of radiolabeled ligand associated with the receptor bound to the HAP pellet fraction. It is expected that arylretinamides that do not compete with all-trans-[$^3$H]-RA for binding to retinoic acid receptors (RARs) and with [$^3$H]-9-cis RA for binding to RXRγ will have fewer toxicities or adverse side effect than arylretinamides that have such binding properties.

A troublesome side effect of 4-HPR is night blindness. This results because 4-HPR competes with the natural circulating form of all-trans retinol (Vitamin A) for binding to serum retinol binding proteins. An arylretinamide having less affinity for serum RBP than 4-HPR is less likely to exhibit this side effect, and is, thus, preferred. Such property is determined using a serum retinol protein binding assay. RBP (human) is obtained commercially (Sigma). RBP (0.1 µg/µl) is incubated with 250 nM all-trans-(3H)-ROL (approx. 5Ci/mmole) with and without competing ligands at 4° C. for 3 hours. Tritiated retinoid-labeled protein-containing extracts are treated with dextran-coated charcoal to remove unbound ligand before subjecting samples to sedimentation analysis on 5 to 20% sucrose density gradients $^{14}$C-Labeled proteins are included with samples as internal sedimentation standards. Gradients are centrifuged at 257,000 g for 20 hours at 4° C. followed by fractionation and analysis of radioactivity Therapeutic Methods In another aspect, the present invention provides methods of treating or preventing cancer in a mammalian subject in need of the same. Although it is possible to use the present methods to treat cancer in all mammalian subjects, the preferred mammalian subject is a human subject. The method comprises administering a biologically effective amount of one or more of the present arylretinamide to the subject. For ease of adminstration the arylretinamide may be formulated into a pharmaceutical composition that comprises one or more of the present arylretinamides and othe non toxic components.

Dosage

As used herein, the term "biologically effective amount" means the total amount of the arylretinamides in the pharmaceutical formulation or method that is sufficient to show a meaningful subject or patient benefit, i.e., a reduction in tumor size, arrest, or inhibition of tumor growth and/or motility or metastasis, and/or an increase in apoptosis, and/or a reduction in the symptoms related to the presence of the tumor. In vitro, the biologically effective amount, i.e. the amount sufficient to induce apoptosis of malignant cells, is administered in two-fold increments, to determine the full range of activity. Thereafter, the biologically effective amount will be evaluated in animal studies. Ultimately, the dosage will be determined using clinical trials. The dosages of the arylretinamide which can treat or prevent the targeted cancer can be determined in view of this disclosure by one of ordinary skill in the art by running routine trials with appropriate controls.

The factors to be considered include the condition being treated, the route of administration, the nature of the formulation, the mammal's body weight, surface area, age and general condition, and the particular compound to be administered. Initially, the attending physician will administer low doses of the composition and observe the patient's response. Larger doses of composition may be administered until the optimal therapeutic effect is obtained for the patient, and at that point the dosage is not increased further.

An effective amount can be achieved by one administration of the composition. Alternatively, an effective amount is achieved by multiple administrations of the composition to the subject. The total daily dose may be given as a single dose, multiple doses, e.g., two to six times per day, or by intravenous infusion for a selected duration.

The duration of therapy with the arylretinamides used in the method of the present invention will vary, depending on the unique characteristics of the arylretinamides being used and the particular therapeutic effect to be achieved, the severity of the disease being treated and the condition and potential idiosyncratic response of each individual patient.

Ultimately the attending physician will decide on the appropriate duration of therapy.

Modes of Administration

The present arylretinamides may be administered prophylactically, chronically, or acutely. For example, such compounds may be administered prophylactically to inhibit the formation of cancers in the subject being treated. The subject compounds may also be administered prophylactically to patients suffering a primary cancer to prevent the occurrence of metastatic cancers. In addition to the prevention of primary and metastatic cancers, chronic administration of the subject compounds will typically be indicated in treating recurring cancers. Acute administration of the subject compounds is indicated to treat, for example, aggressive cancers prior to surgical or radiological intervention.

The arylretinamides of this invention may be administered in a number of ways depending upon whether local or systemic treatment is desired, and upon the area to be treated. Administration may be topical (including ophthalmic, vaginal, rectal, intranasal), oral, or parenteral, for example by intravenous drip, intravenous injection or subcutaneous, intraperitoneal or intramuscular injection. Those skilled in the art will recognize that delivery via local injection contemplates the use of a syringe, catheter or similar device, which delivers the pharmaceutical composition to the target site, i.e., to an area exhibiting neoplasia. Delivery may be direct, i.e., intratumoral, or nearly direct, i.e., intralesional, that is, to an area that is sufficiently close to a tumor so that the active agent exhibits the desired pharmacological activity with respect to the tumor itself. Administration of the arylretinamides, preferably, is oral or topical.

Pharmaceutical Compositions

Another aspect of the invention provides pharmaceutical compositions comprising one or more active arylretinamides or pharmaceutically-acceptable salts thereof, in combination with an acceptable carrier therefor and optionally with other therapeutically-active ingredients or inactive accessory ingredients. The carrier must be pharmaceutically-acceptable in the sense of being compatible with the other ingredients of the formulation and not deleterious to the recipient. Many such carriers are routinely used and can be identified by reference to pharmaceutical texts. The characteristics of the carrier will depend on the route of administration and particular compound or combination of compounds in the composition. Preparation of such formulations is within the level of skill in the art. The composition may further contain other agents which either enhance the activity of the analog or complement its activity. The composition may further comprise fillers, salts, buffers, stabilizers, solubilizers, and other materials well known in the art.

The pharmaceutical compositions include those suitable for oral, topical, inhalation, rectal or parenteral (including subcutaneous, intramuscular and intravenous) administration.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

Formulations suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the arylretinamide which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the subject compounds are preferably utilized at a concentration of from about 0.1% to 5.0% by weight.

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

In general, the pharmaceutical compositions of this invention contain from about 0.5 mg to about 1.5 g active ingredient per unit dose and, preferably, from about 7.5 to about 1000 mg per unit dose. If discrete multiple doses are indicated, treatment might typically be 100 mg of the arylretinamide given from two to four times per day.

The invention may be better understood by reference to the following examples, which serve to illustrate but not to limit the present invention.

EXAMPLES

Methods and Materials for Synthesis

Reagents and aromatic amines were purchased from Sigma-Aldrich. Anhydrous THF was obtained by distillation from sodium benzophenone ketyl. Resins were pre-rinsed with THF and dried under argon; the polymer-suported triphenylphosphine was then dried to completeness under vacuum. TLC was performed on Merck silica gel 60 $F_{254}$ aluminum plates. Merck silica gel 60, 70–230 mesh was utilized for column chromatography. Preparative TLC was performed on Whatman PK5F silica gel plates (1 mm). Melting points were determined using a Thomas-Hoover capillary apparatus and are uncorrected. Ultraviolet-visible absorption data were recorded in methanol using a Beckman DU-40 spectrophotometer. Infrared spectra were recorded as films on silver chloride plates using a Nicolet Protégé460. NMR spectra were recorded on a Bruker DRX 400 operating at 400 MHz for $^1$H measurements in acetone-$d_6$, purchased from Cambridge Isotopes Laboratories. Mass spectra were recorded on a Micromass QTOF electrospray mass spectrometer at the CCIC-Mass Spectometry Facility. Purities were determined on a Beckman System Gold High-Performance Liquid Chromatography Spectrometer using a Beckman Ultrasphere ODS column (5 $\mu$, 4.6 mm×26 cm) in 86:14 MeOH/$H_2$O (1 mL/min, 350 nm).

Preparation of Reactants

A. TBDMS Protection of Benzylalcohol

A dry, 10 mL Reactivial was charged with 1.00 mmol of the appropriate aminobenzylalcohol and 8 mL of dry THF and stirred under argon. Sodium hydride (1.13 mmol, 28.5 mg) was slowly added. When bubbles were no longer detected, 1.22 mmol (184 mg) of tert-butyl-dimethylsilyl-chloride was added and the solution stirred overnight. The cloudy solution was concentrated in vacuuo, reconstituted in ca. 10 mL of EtOAc, washed with water (2×10 mL) and brine (8 mL), dried over $MgSO_4$ and concentrated in vacuuo.

Reactant: (3-aminobenzyl)-tert-butyl-dimethylsilyl ether (i)

Synthesis was performed as described above using 123.1 mg of 3-aminobenzylalcohol. Preparative TLC (65:35 EtOAc/hexanes) afforded 131.4 mg (55.3% yield) of yellow oil having a $^1$H NMR spectrum consistent with the structure of the desired product. $^1$H NMR δ 0.10 (s, 6H, —Si(CH$_3$)$_2$), 0.93 (s, 9H, —SiC(CH$_3$)$_3$), 4.52 (br, 2H, —NH$_2$), 4.62 (s, 2H, Ar—CH$_2$), 6.52–6.57 (m, 2H, 4- and 6-H), 6.66 (s, 1H, 2-H), 6.99 (dd, 1H, 5-H, J=J=7.8 Hz)

Reactant (2-aminobenzyl)-tert-butyl-dimethylsilyl ether (ii)

Synthesis was performed as described above using 123.2 mg of 2-aminobenzylalcohol. Column chromatography (1:1 EtOAc/hexanes) afforded 125.0 mg of crude product as a yellow oil having a $^1$H NMR spectrum consistent with the structure of the desired product. $^1$H NMR δ 0.10 (s, 6H, —Si(CH$_3$)$_2$), 0.93 (s, 9H, —SiC(CH$_3$)$_3$), 4.61 (br, 2H, —NH$_2$), 4.70 (s, 2H, Ar—CH$_2$), 6.59 (dd, 1H, J=J=7.4 Hz), 6.69 (d, 1H, J=7.9 Hz), 7.01 (dd, 1H, J=J=7.6 Hz), 6.08 (dd, 1H, J=J=7.4 Hz).

B. Methylester Formation via Diazomethane

Diazomethane was generated by slowly dripping a solution of Diazald® (3.6 g/75 mL Et$_2$O) into a round-bottom flask containing 1 g of NaOH, 2 mL of water, and 10 mL of ethanol maintained in a 60° C. oil bath. The distilled CH$_2$N$_2$ was trapped in ether maintained at 4° C. and added by pipetfuls to the appropriate benzoic acids (0.45 mmol) until bubbles were no longer detected and/or TLC showed the absence of starting material. Purification was specific for each reaction.

Reactant 3-amino-methylsalicylate (164-A2)

Synthesis was performed as described above using 92.9 mg of 3-aminosalicylic acid. Column chromatography (1:2 Et$_2$O/hexanes) afforded 86.2(85.0% yield) of white solid having a $^1$H NMR spectrum consistent with the structure of the desired product. $^1$H NMR δ 3.91 (s, 3H, —CO$_2$CH$_3$), 4.56 (br, 2H, —NH$_2$), 6.68 (dd, 1H, 5-H, J=J=7.9 Hz), 6.92 (dd, 1H, J=7.7 Hz, J=1.2 Hz), 7.11 (dd, 1H, J=8.0 Hz, J=1.4 Hz), 10.86 (s, 1H, —OH).

Reactant 3-hydroxy-methylanthranilate (164-B)

Synthesis was performed as described above using 68.6 mg of 3-hydroxyanthranilic acid. Column chromatography (1:2 Et$_2$O/hexanes) afforded 47.9 mg (63.3% yield) of solid having a $^1$H NMR spectrum consistent with the structure of the desired product. $^1$H NMR δ 3.81 (s, 3H, —CO$_2$CH$_3$), 6.11 (br, 2H, —NH$_2$), 6.41 (dd, 1H, 5-H, J=8.1 Hz, J=7.7 Hz), 6.88 (dd, 1H, J=.7.6 Hz, J=1.4 Hz), 7.33 (dd, 1H, J=8.2 Hz, J=1.4 Hz), 8.58 (br, 1H, —OH).

Reactant 4-amino-methylsalicylate (164-D2)

Synthesis was performed as described above using 91.0 mg of 4-aminosalicylic acid. Column chromatography (29:20 EtOAc/hexanes) afforded 79.6 mg (80.2% yield) of whitish solid having a $^1$H NMR spectrum consistent with the structure of the desired product. $^1$H NMR δ 3.82 (s, 3H, —CO$_2$CH$_3$), 5.51 (br, 2H, —NH$_2$), 6.14 (d, 1H, 3-H, J=2.1 Hz), 6.21 (dd, 1H, 5-H, J=8.7 Hz, J=2.1 Hz), 7.52 (d, 1H, 6-H, J=8.6 Hz), 10.92 (s, 1H, —OH).

Reactant Methyl anthranilate (164-G)

Synthesis was performed as described above using 62.2 mg of anthranilic acid. Column chromatography (1:2 Et$_2$O/hexanes) afforded 62.0 mg (90.4% yield) of colorless oil having a $^1$H NMR spectrum consistent with the structure of the desired product. $^1$H NMR δ 3.81 (s, 3H, —CO$_2$CH$_3$), 6.43 (br, 2H, —NH$_2$), 6.55 (m, 1H), 6.79 (d, 1H, J=8.2 Hz), 7.24 (m, 1H), 7.77 (d, 1H, J=7.8 Hz). C. Methylester formation via acid catalysis Hydrochloric acid gas, generated by dripping concentrated H$_2$SO$_4$ into a flask containing NaCl, was bubbled into a stirring a solution of the appropriate benzoic acid (0.6 mmol) in methanol with slight heating. Purification was specific for each reaction.

Reactant 3-amino-4-hydroxymethylbenzoate (164-C2)

Synthesis was performed as described above using 93.8 mg of 3-amino-4-hydroxybenzoic acid. Column chromatography (5:3 EtOAc/hexanes) afforded 71.6 mg (69.9% yield) of white and red solid having a $^1$H NMR spectrum consistent with the structure of the desired product. $^1$H NMR δ 3.77 (s, 3H, —CO$_2$CH$_3$), 3.78 (br, 2H, —NH$_2$), 6.78 (d, 1H, 5-H, J=8.2 Hz), 7.21 (dd, 1H, 6-H, J=8.2 Hz, J=2.0 Hz), 7.37 (d, 1H, J=2.0 Hz).

Reactant 4-amino-3-hydroxymethylbenzoate (164-E2)

Synthesis was performed as described above using 92.0 mg of 4-amino-3-hydroxybenzoic acid to afford 107.6 mg of crude product having a $^1$H NMR spectrum consistent with the structure of the desired product. $^1$H NMR δ 3.75 (s, 3H, —CO$_2$CH$_3$), 4.95 (br, 2H, —NH$_2$), 6.69 (d, 1H, 5-H, J=8.2 Hz), 7.36–7.40 (m, 2H, 5- and 6-H), 8.50 (br, 1H, —OH).

Reactant 5-amino-methylsalicylate (164-F2)

Synthesis was performed as described above using 92.9 mg of 5-amino-salicylic acid. Aqueous work-up with IN NaHCO$_3$ yielded 38.1 g of crude product having a $^1$H NMR spectrum consistent with the structure of the desired product. $^1$H NMR δ 3.89 (s, 3H, —CO$_2$CH$_3$), 4.38 (br, 2H, —NH$_2$), 6.72 (d, 1H, 3-H, J=8.8 Hz), 6.92 (dd, 1H, 4-H, J=8.8 Hz, J=2.9 Hz), 7.12 (d, 1H, 6-H, J=2.9 Hz), 10.42 (s, 1H, —OH).

Reactant 2-Amino-5-azidophenol hydrochloride

A solution of 2-amino-5-nitrophenol (5.0 g) in pyridine (100 mL) was treated as previously described to give 3-hydroxy-4-trifluoroacetamidoaniline. The crude product was purified by a series of acid-base extractions to yield 4.9 g of a dark brown solid. A sample of this product (1.0 g) was dissolved in 1 N HCl (50 mL), cooled to 0° C., and treated with a chilled aqueous solution of NaNO$_2$ (470 mg). This mixture was stirred at 0° C. for 30 min and then treated with a cold aqueous solution of NaN$_3$ (443 mg). The resulting precipitate was filtered, washed with water, and dried to yield 830 mg of a brown solid. The solid was dissolved in 1 N HCl and refluxed for 12 h. The reaction mixture was then concentrated under reduced pressure to yield the title compound as the hydrochloride salt.

Example 1

Preparation of Arylretinamides

A dry, 10 mL Reactivial (Pierce Chemical Co.) was charged with 0.2 mmol (60 mg) of RA, 0.6 meq (200 mg) of resin-bound triphenylphoshine (~3 mmol 31P/g resin), and 6 mL of dry THF and stirred under argon. The vial was placed in an ice bath and 16 µL (0.11 mmol) of hexachloroacetone was added to the solution, which turned dark red within 1 min. After stirring at 0° C. for 1 h, 0.3 mmol of the selected aromatic amine, ca. 3 mL of dry THF, and 100 µL (1.24 mmol, unless indicated otherwise) of pyridine were added in rapid succession. Formation of pyridine salts was observed. The reaction mixture was removed from the ice bath and allowed to warm to room temperature. After stirring for 1–2 h, the product mixture was vacuum filtered to remove the resin and rinsed with dry THF. The filtrate was concentrated in vacuuo and transferred back into the Reactivial (maintained under argon) using ca. 7.5 mL of dry THF. Tetrafluorophthalic anhydride (0.25 mmol) was added and the mixture stirred for 20–25 min. Deionized water (35 µL) was then added, the solution stirred for 15 min, and ca. 2.8 meq of Amberlite A-21 ion-exchange resin (4.7 meq/g resin)

and ca. 1.5 mL of THF were added. The mixture was stirred for 1 h. The resin was removed by vacuum filtration and rinsed several times with THF. The filtrate was concentrated, and subjected to chromatographic purification specific for each product mixture.

Comparative Examples

Comparative Example A

N-(4'-hydroxyphenyl)retinamide (41)

Synthesis was performed as described above using 33.2 mg of p-aminophenol. Column chromatography (2:3 EtOAc/hexanes) afforded 73.7 mg (94.1% yield) of yellow solid, m.p. 145.5–147.5° C. UV-Vis $\lambda_{max}$ 362 nm ($\epsilon$ 48,389); $^1$H NMR $\delta$ 1.03 (s, 6H, 16- and 17-CH$_3$), 1.46–1.48 (m, 2H, 2-H), 1.58–1.63 (m, 2H, 3-H), 1.70 (s, 3H, 18-CH$_3$), 2.01–2.03 (m, 4H, 4-H and 19-CH$_3$), 2.41 (s, 3H, 20-CH$_3$), 5.99 (s, 1H, 14-H), 6.15–6.36 (m, 4H, vinyls), 6.76 (d, 2H, 3'-H, J=8.8 Hz), 7.04 (dd, 1H, 11-H, J=15.0 Hz, J=11.4 Hz), 7.54 (d, 2H, 2'-H, J=8.7 Hz), 8.11 (s, 1H, X—H), 9.00 (s, 1H, X—H); $^{13}$C NMR $\delta$ 12.83, 13.48, 19.86, 21.91, 29.24, 33.57, 34.84, 40.30, 115.89, 121.60, 123.69, 128.51, 130.06, 130.27, 130.98, 132.87, 137.09, 138.49, 138.55, 139.00, 149.24, 154.22, 164.24

Comparative Example B

N-(2'-hydroxy-4'-carboxymethylphenyl)retinamide (42)

Synthesis was performed as described in General Procedure A using 2 mL of 71.6 mg 164-C2/2.8 mL THF. Column chromatography (1:3 EtOAc/hexanes) afforded 92.8 mg of crude yellow solid. UV-Vis $\lambda_{max}$ 365.5 nm ($\epsilon$ 34,922); $^1$H NMR $\delta$ 1.03 (s, 6H, 16- and 17-CH$_3$), 1.46–1.50 (m, 2H, 2-H), 1.59–1.63 (m, 2H, 3-H), 1.71 (s, 3H, 18-CH$_3$), 2.01–2.04 (m, 4H, 4-H and 19-CH$_3$), 2.44 (s, 3H, 20-CH$_3$), 3.82 (s, 3H, —CO$_2$CH$_3$), 6.19–6.42 (m, 5H, vinyls), 6.97 (d, 1H, 3'-H, J=8.5 Hz), 7.16 (dd, 1H, 11-H, J=15.0 Hz, J=11.5 Hz), 7.68 (dd, 1H, 4'-H, J=8.4 Hz, J=1.9 Hz), 8.23 (d, 1H, 6'-H, J=1.7 Hz), 9.32 (s, 1H, X—H), 10.60 (s, 1H, X—H); $^{13}$C NMR $\delta$ 12.98, 13.80, 19.85, 21.91, 29.23, 33.58, 34.84, 40.30, 51.98, 118.26, 118.46, 121.31, 122.60, 124.26, 127.98, 129.09, 130.29, 130.83, 131.83, 136.51, 138.39, 138.52, 140.14, 152.52, 153.60, 166.72, 167.65

Comparative Example C

N-(4'-ethoxyphenyl)retinamide (45)

Synthesis was performed as described above using 44.8 mg of phenetidine. Column chromatography (1:3 EtOAc/hexanes) afforded 52.7 mg (62.8% yield) of yellow solid, m.p. 158–159° C. UV-Vis $\lambda_{max}$ 363 nm ($\epsilon$ 52,030); $^1$H NMR $\delta$ 1.03 (s, 6H, 16- and 17-CH$_3$), 1.31 (t, 3H, —OCH$_2$CH$_3$, J=7.0 Hz), 1.46–1.49 (m, 2H, 2-H), 1.59–1.65 (m, 2H, 3-H), 1.70 (s, 3H, 18-CH$_3$), 2.02–2.04 (m, 4H, 4-H and 19-CH$_3$), 2.41 (s, 3H, 20-CH$_3$), 4.00 (q, 2H, —OCH$_2$CH$_3$, J=7.0 Hz), 5.99 (s, 1H, 14-H), 6.15–6.36 (m, 4H, vinyls), 6.84 (d, 2H, 3'-H, J=9.0 Hz), 7.05 (dd, 1H, 1-H, J=15.0 Hz, J=11.4 Hz), 7.62 (d, 2H, 2'-H, J=8.9 Hz), 9.05 (s, 1H, X—H); $^{13}$C NMR $\delta$ 12.83, 13.48, 15.12, 19.86, 21.90, 29.23, 33.57, 34.85, 40.31, 64.05, 115.17, 121.37, 123.57, 128.56, 130.09, 130.38, 130.98, 133.82, 137.06, 138.49, 138.57, 139.09, 149.46, 155.93, 165.30

Comparative Example D

N-[2'-(carboxymethyl)phenyl] retinamide (43)

Synthesis was performed as described in General Procedure A using 2 mL of 58.2 mg 164-G/2.5 mL THF. Column chromatography (1:3 Et$_2$O/hexanes) afforded 55.6 mg (63.5% yield) of yellow oil. $^1$H NMR $\delta$ 1.03 (s, 6H, 16- and 17-CH$_3$), 1.46–1.49 (m, 2H, 2-H), 1.59–1.63 (m, 2H, 3-H), 1.71 (s, 3H, 18-CH$_3$), 2.01–2.03 (m, 4H, 4-H and 19-CH$_3$), 2.43 (s, 3H, 20-CH$_3$), 3.93 (s, 3H, —CO$_2$CH$_3$), 6.00 (s, 1H, 14-H), 6.17–6.35 (m, 3H, 7-, 8-, and 10-H), 6.50 (d, 1H, 12-H, J=15.1 Hz), 7.09–7.16 (m, 2H, 11- and Ar—H), 7.58 (ddd, 1H, Ar—H, J=J=7.9 Hz, J=1.3 Hz), 8.02 (dd, 1H, Ar—H, J=8.0, J=1.3 Hz), 8.82 (d, 1H, Ar—H, J=8.4 Hz), 11.07 (s, 1H, X—H);

Comparative Example E

N-(2'-carboxyphenyl)retinamide (44)

Potassium hydroxide (0.8 mL of 5N) was added to a solution of 50.7 mg of ZP in methanol/THF (ca. 9 mL) and the mixture stirred for 48 h. Aqueous workup with 1N HCl followed by preparative TLC (EtOAc) afforded 36.5 mg (74.4% yield) of yellow solid, m.p135–136.5° C. UV-Vis $\lambda_{max}$ 367 nm ($\neq$ 46,918); $^1$H NMR $\delta$ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.03–2.07 (m, 4H, 4-H and 19-CH$_3$), 2.42 (s, 3H, 20-CH$_3$), 5.99 (s, 1H, 14-H), 6.16–6.34 (m, 3H, 7-, 8-, and 10-H), 6.46 (d, 1H, 12-H, J=15.1 Hz), 7.07–7.14 (m, 2H, 11- and Ar—H), 7.56 (dd, 1H, Ar—H, J=J=7.7 Hz), 8.11 (d, 1H, Ar—H, J=7.8 Hz), 8.84 (d, 1H, Ar—H, J=8.4 Hz), 11.52 (s, 1H, X—H); $^{13}$C NMR $\delta$ 12.87, 13.63, 19.87, 21.92, 29.24, 33.58, 34.85, 40.31, 116.38, 120.40, 122.76, 123.55, 128.79, 130.17, 130.98, 131.20, 132.28, 134.85, 136.77, 138.50, 139.57, 143.43, 151.22, 165.81, 170.91

Example 2

N-(3'-chloro-4'-hydroxyphenyl)retinamide (11)

Synthesis was performed as described in Example 1 using 43.2 mg of 4-amino-2-chlorophenol. Column chromatography (35:65 EtOAc/hexanes) afforded 59.5 mg (69.9% yield) of yellow solid, m.p. 168–169° C. UV-Vis $\lambda_{max}$ 363.5 nm ($\epsilon$ 53,752); $^1$H NMR $\delta$ 1.01 (s, 6H, 16- and 17-CH$_3$), 1.45–1.47 (m, 2H, 2-H), 1.59–1.63 (m, 2H, 3-H), 1.69 (s, 3H, 18-CH$_3$), 2.00–2.03 (m, 4H, 4-H and 19-CH$_3$), 2.39 (s, 3H, 20-CH$_3$), 5.95 (s, 1H, 14-H), 6.15–6.34 (m, 4H, vinyls), 6.91 (d, 1H, 5'-H, J=8.8 Hz), 7.05 (dd, 1H, 11-H, J=15.0 Hz, J=11.4 Hz), 7.35 (d, 1H, 6'-H, J=8.7 Hz), 7.92 (s, 1H, 2'-H), 8.45 (s, 1H, X—H), 9.10 (s, 1H, X—H); $^{13}$C NMR 67 12.84, 13.54, 19.87, 21.90, 29.24, 33.58, 34.86, 40.32, 117.36, 119.93, 120.59, 121.52, 123.11, 128.68, 130.14, 130.69, 130.94, 133.82, 136.90, 138.48, 138.57, 139.31, 149.59, 150.07, 165.44; MS m/e (relative intensity) 448 (M$^+$, 100); HRMS calcd for C$_{26}$H$_{32}$NO$_2$Cl (M+Na) 448.2019, found 448.2049

Example 3

N-(3',5'-dichloro-4'-hydroxyphenyl)retinamide (13)

Synthesis was performed as described in Example 1 using 54.8 mg of 4-amino-2,6-dichlorophenol. Column chromatography (1:4 EtOAc:hexanes) afforded 70.0 mg (75.2% yield) of yellow solid, m.p. 139–140° C. UV-Vis $\lambda_{max}$ 366 nm ($\epsilon$ 54,229); $^1$H NMR $\delta$ 1.03 (s, 6H, 16- and 17-CH$_3$), 1.46–1.49 (m, 2H, 2-H), 1.60–1.63 (m, 2H, 3-H), 1.70 (s, 3H, 18-CH$_3$), 2.02–2.05 (m, 4H, 4-H and 19-CH$_3$), 2.41 (s, 3H, 20-CH$_3$), 5.95 (s, 1H, 14-H), 6.15–6.37 (m, 4H, vinyls), 7.10 (dd, 1H, 11-H, J=15.0 Hz, J=11.4 Hz), 7.76 (s, 2H, 2'- and 6'-H), 8.55 (br, 1H, X—H), 9.24 (s, 1H, X—H); $^{13}$C NMR $\delta$ 12.85, 13.60, 19.86, 21.90, 29.23, 33.58, 34.85, 40.31, 120.00, 122.50, 122.57, 128.83, 130.19, 130.88, 131.08, 133.96, 136.70, 138.44, 138.55, 139.59, 145.68, 150.85, 165.66; MS, m/e (relative intensity) 482 (M$^+$, 100); HRMS calcd for C$_{26}$H$_{31}$NO$_2$Cl$_2$ (M+Na) 482.1630, found 482.1637

Example 4

N-(5'-chloro-2'-hydroxyphenyl)retinamide (12)

Synthesis was performed as described in Example 1 using 43.0 mg of 2-amino-4-chlorophenol. Column chromatography (1:4 EtOAc/hexanes) followed by preparative TLC (1:4 EtOAc/hexanes) afforded 50.0 mg (59.0% yield) of yellow solid, m.p. 115–118° C. UV-Vis $\lambda_{max}$ 368 nm ($\epsilon$ 40,128); $^1$H NMR (acetone-$d_6$) δ 1.03 (s, 6H, 16- and 17-CH$_3$), 1.46–1.49 (m, 2H, 2-H), 1.59–1.63 (m, 2H, 3-H), 1.70 (s, 3H, 18-CH$_3$), 2.01–2.05 (m, 4H, 4-H and 19-CH$_3$), 2.43 (s, 3H, 20-CH$_3$), 6.17–6.41 (m, 5H, vinyls), 6.89 (d, 1H, 3'-H, J=8.6 Hz), 6.99 (dd, 1H, 4'-H, J=8.6 Hz, J=2.6 Hz), 7.15 (dd, 1H, 11-H, J=15.0 Hz, J=11.4 Hz), 7.80 (d, 1H, 6'-H, J=2.4 Hz), 9.06 (s, 1H, X—H), 9.59 (br, 1H, X—H); $^{13}$C NMR δ 12.86, 13.75, 19.84, 21.89, 29.22, 33.57, 34.84, 40.29, 119.01, 121.63, 121.75, 124.56, 125.27, 129.03, 129.28, 130.26, 130.83, 131.66, 136.53, 138.40, 138.53, 140.01, 147.60, 152.17, 167.13; MS m/e (relative intensity) 448 (M$^+$, 100); HRMS calcd for C$_{26}$H$_{32}$NO$_2$Cl (M+Na) 448.2019, found 448.2010

Example 5

N-(2'-chloro-4'-hydroxyphenyl)retinamide (10)

Synthesis was performed as described in Example 1 using 54.0 mg of 4-amino-3-chlorophenol hydrochloride. Column chromatography (2:3 EtOAc/hexanes) afforded 63.6 mg (74.6% yield) of yellow solid, m.p. 131.5–132.5° C. UV-Vis $\lambda_{max}$ 358 nm ($\epsilon$ 52,476); $^1$H NMR δ 1.03 (s, 6H, 16- and 17-CH$_3$), 1.46–1.49 (m, 2H, 2-H), 1.59–1.65 (m, 2H, 3-H), 1.70 (s, 3H, 18-CH$_3$), 2.02–2.05 (m, 4H, 4-H and 19-CH$_3$), 2.40 (s, 3H, 20-CH$_3$), 6.15–6.37 (m, 5H, vinyls), 6.80 (dd, 1H, 4'-H, J=8.9 Hz, J=2.7 Hz), 6.91 (d, 1H, 3'-H, J=2.7 Hz), 7.08 (dd, 1H, 11-H, J=15.0 Hz, J=11.4 Hz), 7.92 (d, 1H, 5'-H, J=8.3 Hz), 8.44 (s, 1H, X—H), 8.62 (s, 1H, X—H); $^{13}$C NMR δ 12.85, 13.61, 19.87, 21.91, 29.23, 33.57, 34.85, 40.31, 115.10, 116.47, 122.94, 126.47, 128.55, 128.68, 130.13, 130.74, 130.95, 136.91, 138.50, 138.57, 139.32, 150.29, 155.44, 165.58; MS m/e (relative intensity) 448 (M$^+$, 100); HRMS calcd for C$_{26}$H$_{32}$NO$_2$Cl (M+Na) 448.2019, found 448.2025

Example 6

N-(3',5'-dichloro-2'-hydroxy-4'-methylphenyl)retinamide (15)

Synthesis was performed as described in Example 1 using 68.8 mg of 6-amino-2,4-dichloro-3-methylphenol hydrochloride. Column chromatography (1:2:7 toluene/Et$_2$O/hexanes) afforded 29.5 mg (31.1% yield) of orange solid, m.p. 140–142° C. UV-Vis $\lambda_{max}$ 368.5 nm ($\epsilon$ 46,347); $^1$H NMR δ 1.03 (s, 6H, 16- and 17-CH$_3$), 1.46–1.49 (m, 2H, 2-H), 1.59–1.63 (m, 2H, 3-H), 1.71 (s, 3H, 18-CH$_3$), 2.01–2.04 (m, 4H, 4-H and 19-CH$_3$), 2.39 (s, 3H, Ar—CH$_3$), 2.43 (s, 3H, 20-CH$_3$), 6.17–6.41 (m, 5H, vinyls), 7.18 (dd, 1H, 11-H, J=15.0 Hz, J=11.4 Hz), 7.55 (s, 1H, 5'-H), 9.40 (s, 1H, X—H); $^{13}$C NMR δ 12.89, 13.86, 17.55, 19.86, 21.91, 29.23, 33.60, 34.86, 40.32, 120.87, 120.96, 124.95, 127.57, 129.24, 130.36, 130.80, 131.40, 132.16, 136.36, 138.37, 138.53, 140.39, 144.90, 159.27, 167.87; MS m/e (relative intensity) 496 (M$^+$, 100); HRMS calcd for C$_{27}$H$_{33}$NO$_2$Cl$_2$ (M+Na) 496.1786, found 496.1790

Example 7

N-(2'-hydroxy-5'-methylphenyl)retinamide (4)

Synthesis was performed as described in Example 1 using 37.5 mg of 2-amino-p-cresol. Column chromatography (45:55 Et$_2$O/hexanes) afforded 64.7 mg (79.8% yield) of orange solid, m.p. 98–100° C. UV-Vis max 367 nm ($\epsilon$ 42,810); $^1$H NMR δ 1.03 (s, 6H, 16- and 17-CH$_3$), 1.46–1.49 (m, 2H, 2-H), 1.60–1.63 (m, 2H, 3-H), 1.71 (s, 3H, 18-CH$_3$), 2.01–2.05 (m, 4H, 4-H and 19-CH$_3$), 2.20 (s, 3H, Ar—CH$_3$), 2.43 (s, 3H, 20-CH$_3$), 6.17–6.41 (m, 5H, vinyls), 6.78 (d, 1H, 3'-H, J=8.2 Hz), 6.84 (dd, 1, 4'-H, J=8.1 Hz, J=1.6 Hz), 7.11–7.18 (m, 2H, 11- and 6'-H), 9.20–9.22 (m, 1H, X—H), 9.37–9.39 (m, 1H, X—H); $^{13}$C NMR δ 12.88, 13.74, 19.87, 20.47, 21.91, 29.24, 33.59, 34.86, 40.32, 119.02, 121.61, 123.23, 127.25, 127.49, 128.99, 129.59, 130.26, 130.87, 131.53, 136.62, 138.43, 138.55, 139.92, 147.53, 151.78, 167.40; MS m/e (relative intensity) 428 (M$^+$, 100); HRMS calcd for C$_{27}$H$_{35}$NO$_2$ (M+Na) 428.2565, found 428.2562

Example 8

N-(2'-hydroxy-6'-methylphenyl)retinamide (6)

Synthesis was performed as described in Example 1 using 38.7 mg of 2-amino-m-cresol. Column chromatography (1:3 EtOAc/hexanes) followed by preparative TLC (1:4 EtOAc/hexanes) afforded 66.4 mg (82.9% yield) of red oil. UV-Vis $\lambda_{max}$ 354 nm ($\epsilon$ 42,308); $^1$H NMR δ 1.04 (s, 6H, 16- and 17-CH$_3$), 1.46–1.49 (m, 2H, 2-H), 1.59–1.64 (m, 2H, 3-H), 1.71 (s, 3H, 18-CH$_3$), 2.01–2.04 (m, 4H, 4-H and 19-CH$_3$), 2.30 (s, 3H, Ar—CH$_3$), 2.44 (s, 3H, 20-CH$_3$), 6.17–6.41 (m, 5H, vinyls), 6.73–6.79 (m, 2H, 3'- and 5'-H), 7.01 (dd, 1H, 4'-H, J=J=7.8 Hz), 7.14 (dd, 1H, 11-H, J=15.0 Hz, J=11.4 Hz), 8.68 (s, 1H, X—H), 8.87 (s, 1H, X—H); $^{13}$C NMR δ 12.95, 13.82, 18.52, 19.91, 21.98, 29.30, 33.63, 34.89, 40.34, 117.59, 121.48, 122.60, 126.06, 127.65, 129.02, 130.28, 130.89, 131.54, 133.66, 136.64, 138.43, 138.56, 139.90, 151.75, 152.58, 167.88; MS m/e (relative intensity) 428 (M$^+$, 100); HRMS calcd for C$_{27}$H$_{35}$NO$_2$ (M+Na) 428.2565, found 428.2552

Example 9

N-(2'-hydroxy-4'-methylphenyl)retinamide (3)

Synthesis was performed as described in Example 1 using 37.0 mg of 6-amino-m-cresol. Column chromatography (45:55 Et$_2$O/hexanes) afforded 53.8 mg (66.3% yield) of yellow solid, m.p. 146–147.5° C. IR (cm$^{-1}$). UV-Vis $\lambda_{max}$ 366 nm ($\epsilon$ 55,590); $^1$H NMR δ 1.03 (s, 6H, 16- and 17-CH$_3$), 1.46–1.49 (m, 2H, 2-H), 1.59–1.64 (m, 2H, 3-H), 1.71 (s, 3H, 18-CH$_3$), 2.01–2.05 (m, 4H, 4-H and 19-CH$_3$), 2.30 (s, 3H, Ar—CH$_3$), 2.44 (s, 3H, 20-CH$_3$), 6.17–6.40 (m, 5H, vinyls), 6.62 (dd, 1, 5'-H, J=8.1 Hz, J=1.3 Hz), 6.72 (br, 1, 3'-H), 7.10–7.19 (m, 2H, 11- and 6'-H), 9.29 (br, 1H, X—H), 9.66 (br, 1H, X—H); $^{13}$C NMR δ 12.88, 13.73, 19.86, 20.81, 21.91, 29.24, 33.59, 34.86, 40.32, 119.85, 121.18, 121.53, 122.85, 125.29, 128.99, 130.26, 130.86, 131.50, 136.63, 136.67, 138.42, 138.55, 139.91, 149.75, 151.72, 167.41; MS m/e (relative intensity) 428 (M$^+$, 100); HRMS calcd for C$_{27}$H$_{35}$NO$_2$ (M+Na) 428.2565, found 428.2557

Example 10

N-(3'-hydroxy-2'-methylphenyl)retinamide (8)

Synthesis was performed as described in Example 1 using 37.2 mg of 3-amino-o-cresol. Column chromatography (2:3 EtOAc/hexanes) afforded 57.2 mg (70.5% yield) of white solid, m.p. 176–176.5° C. UV-Vis $\lambda_{max}$ 357.5 nm ($\epsilon$ 49,601); $^1$H NMR δ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.02–2.05 (m, 4H, 4-H and 19-CH$_3$), 2.12 (s, 3H, Ar—CH$_3$), 2.40 (s, 3H, 20-CH$_3$), 6.15–6.38 (m, 5H, vinyls), 6.66 (d, 1H, Ar—H, J=8.0 Hz), 6.95 (dd, 1H, 5'-H, J=J=8.0 Hz), 7.28

(br, 1H, Ar—H), 8.23 (s, 1H, X—H), 8.46 (br, 1H, X—H); $^{13}$C NMR δ 10.50, 12.84, 13.56, 19.87, 21.91, 29.24, 33.57, 34.86, 40.31, 112.04, 116.30, 123.55, 126.45, 128.56, 130.08, 130.41, 131.00, 137.08, 138.52, 138.58, 138.93, 139.08, 149.53, 156.31, 165.60; MS m/e (relative intensity) 428 (M$^+$, 100); HRMS calcd for $C_{27}H_{35}NO_2$ (M+Na) 428.2565, found 428.2562

Example 11

N-(2'-methyl-4'-hydroxyphenyl)retinamide (1)

Synthesis was performed as described in Example 1 using 37.8 mg of 4-amino-m-cresol. Column chromatography (3:1 EtOAc/hexanes) followed by preparative TLC (65:35 EtOAc/hexanes) afforded 57.7 mg (71.1% yield) of orange solid, m.p. 141–145° C. UV-Vis $\lambda_{max}$ 356 nm (ε 49,722); $^1$H NMR δ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.02–2.04 (m, 4H, 4-H and 19-CH$_3$), 2.17 (s, 3H, Ar—CH$_3$), 2.39 (s, 3H, 20-CH$_3$), 6.11–6.38 (m, 5H, vinyls), 6.61 (dd, 1, 5'-H, J=8.4 Hz, J=2.3 Hz), 6.67 (br, 1H, 3'-H), 7.04 (dd, 1H, 11-H, J=15.0 Hz, J=11.4 Hz), 7.37 (d, 1H, 6'-H, J=8.5 Hz), 8.12 (s, 1H, X—H), 8.42 (s, 1H, X—H); $^{13}$C NMR δ 12.83, 13.52, 18.34, 19.85, 21.91, 29.23, 33.55, 34.82, 40.28, 113.37, 117.51, 123.58, 126.91, 128.45, 129.51, 130.02, 130.19, 130.98, 133.97, 137.11, 138.48, 138.53, 138.90, 149.03, 155.57, 165.78; MS m/e (relative intensity) 428 (M$^+$, 100); HRMS calcd for $C_{27}H_{35}NO_2$ (M+Na) 428.2565, found 428.2562

Example 12

N-(3'-hydroxy-4'-methylphenyl)retinamide (7)

Synthesis was performed as described in Example 1 using 37.4 mg of 5-amino-o-cresol. Column chromatography (35:65 EtOAc/hexanes) afforded 65.1 mg (80.31% yield) of yellow solid, m.p. 172.5–175° C. UV-Vis $\lambda_{max}$ 364 nm (ε 54,492); $^1$H NMR δ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.02–2.05 (m, 4H, 4-H and 19-CH$_3$), 2.13 (s, 3H, Ar—CH$_3$), 2.40 (s, 3H, 20-CH$_3$), 5.99 (s, 1H, 14-H), 6.15–6.35 (m, 4H, vinyls), 6.95 (m, 2H, 5'- and 6'-H), 7.05 (dd, 1H, 11-H, J=15.0 Hz, J=11.4 Hz), 7.46 (s, 1H, 2'-H), 8.11 (s, 1H, X—H), 9.01 (br, 1H, X—H); $^{13}$C NMR δ 12.84, 13.50, 15.68, 19.87, 21.91, 29.24, 33.57, 34.85, 40.31, 106.85, 111.06, 119.78, 123.60, 128.60, 130.11, 130.46, 130.97, 131.22, 137.04, 138.49, 138.57, 139.14, 139.46, 149.62, 156.10, 165.48; MS m/e (relative intensity) 428 (M$^+$, 100); HRMS calcd for $C_{27}H_{35}NO_2$ (M+Na) 428.2565, found 428.2567

Example 13

N-(4'-hydroxy-2',5'-dimethylphenyl)retinamide (2)

Synthesis was performed as described in Example 1 using 42.5 mg of 4-amino-2,5-dimethylphenol. Column chromatography (1:1 EtOAc/hexanes) afforded 73.1 mg (84.81% yield) of yellow solid, decomposed at 160° C. UV-Vis $\lambda_{max}$ 356 nm (ε 51,362); $^1$H NMR δ 1.03 (s, 6H, 16- and 17-CH$_3$), 1.46–1.49 (m, 2H, 2-H), 1.59–1.63 (m, 2H, 3-H), 1.70 (s, 3H, 18-CH$_3$), 2.01–2.05 (m, 4H, 4-H and 19-CH$_3$), 2.13 (s, 3H, Ar—CH$_3$), 2.39 (s, 3H, 20-CH$_3$), 6.01–6.38 (m, 5H, vinyls), 6.65 (s, 1H, Ar—H), 7.04 (dd, 1H, 11-H, J=15.1 Hz, J=11.4 Hz), 7.29–7.31 (m, 1H, Ar—H), 7.92 (s, 1H, X—H), 8.33 (br, 1H, X—H); $^{13}$C NMR δ 12.82, 13.48, 15.83, 17.90, 19.87, 21.90, 29.23, 33.56, 34.85, 40.30, 116.95, 122.18, 123.76, 128.19, 128.45, 129.38, 130.03, 130.13, 130.91, 131.02, 137.20, 138.53, 138.87, 148.87, 153.42, 165.58; MS m/e (relative intensity) 442 (M$^+$, 100); HRMS calcd for $C_{28}H_{37}NO_2$ (M+Na) 442.2722, found 442.2698

Example 14

N-(3'-hydroxy-4'-methoxyphenyl)retinamide (9)

Synthesis was performed as described in Example 1 using 41.7 mg of 5-amino-2-methoxyphenol. Column chromatography (3:2 EtOAc/hexanes) followed by preparative TLC (1:1 EtOAc/CH$_2$Cl$_2$) afforded 55.6 mg (65.9% yield) of yellow solid, m.p. 119–124° C. UV-Vis $\lambda_{max}$ 364.5 nm (ε 55,841); $^1$H NMR δ 1.03 (s, 6H, 16- and 17-CH$_3$), 1.46–1.49 (m, 2H, 2-H), 1.60–1.63 (m, 2H, 3-H), 1.70 (s, 3H, 18-CH$_3$), 2.01–2.05 (m, 4H, 4-H and 19-CH$_3$), 2.40 (s, 3H, 20-CH$_3$), 3.80 (s, 3H, Ar—OCH$_3$), 5.98 (s, 1H, 14-H), 6.15–6.35 (m, 4H, vinyls), 6.84 (d, 1H, 5'-H, J=8.7 Hz), 7.05 (dd, 1H, 11-H, J=15.0 Hz, J=11.4 Hz), 7.13 (d, 1H, 6'-H, J=8.7), 7.35 (s, 1H, 2'-H), 7.55 (s, 1H, X—H), 8.98 (br, 1H, X—H); $^{13}$C NMR δ 12.85, 13.50, 19.88, 21.92, 29.25, 33.58, 34.86, 40.32, 56.55, 107.99, 111.05, 112.67, 123.67, 128.56, 130.40, 130.37, 131.00, 134.70, 137.08, 138.51, 138.58, 139.08, 144.48, 147.41, 149.43, 165.31; MS m/e (relative intensity) 444 (M$^+$, 100); HRMS calcd for $C_{27}H_{35}NO_3$ (M+Na) 444.2515, found 444.2502

Example 15

N-(4'-ethylsulfonyl-2'-hydroxyphenyl)retinamide (30)

Synthesis was performed as described in Example 1 using 64.3 mg of 2-amino-4-(ethylsulfonyl)phenol. Column chromatography (2:9 EtOAc/CH$_2$Cl$_2$) afforded 73.0 mg (75.4% yield) of yellow solid, m.p. 145–147° C. UV-Vis $\lambda_{max}$ 366.5 nm (ε 53,266); $^1$H NMR δ 1.03 (s, 6H, 16- and 17-CH$_3$), 1.18 (t, 3H, —SO$_2$CH$_2$CH$_3$, J=7.4 Hz), 1.46–1.49 (m, 2H, 2-H), 1.59–1.63 (m, 2H, 3-H), 1.71 (s, 3H, 18-CH$_3$), 2.01–2.05 (m, 4H, 4-H and 19-CH$_3$), 2.44 (s, 3H, 20-CH$_3$), 3.12 (q, 2H, —SO$_2$CH$_2$, J=7.4 Hz), 6.17–6.42 (m, 5, vinyls), 7.09 (d, 1, 6'-H, J=8.5 Hz), 7.17 (dd, 1H, 11-H, J=15.0 Hz, J=11.4 Hz), 7.52 (dd, 1H, 5'-H, J=8.5 Hz, J=2.3 Hz), 8.28 (d, 1, 3'-H, J=2.2 Hz), 9.25 (s, 1H, X—H), 10.65 (br, 1H, X—H); $^{13}$C NMR δ 7.89, 12.90, 13.84, 19.87, 21.92, 29.25, 33.60, 34.86, 40.32, 51.07,118.20, 121.37, 122.52, 126.23, 128.52, 129.15, 130.33, 130.84, 130.92, 131.93, 136.49, 138.41, 138.55, 140.23, 152.73, 153.16, 167.52; MS m/e (relative intensity) 506 (M$^+$, 100); HRMS calcd for $C_{28}H_{37}NO_4S$ (M+Na) 506.2341, found 506.2349

Example 16

N-(4'-hydroxy-2'-nitrophenyl)retinamide (16)

Synthesis was performed as described in Example 1 using 46.3 mg of 4-amino-3-nitrophenol. Aqueous work-up followed by preparative TLC (1:5 EtOAc/CH$_2$Cl$_2$) afforded 61.4 mg (70.3% yield) of red solid, m.p. 112–117° C. UV-Vis $\lambda_{max}$ 360.5 nm (ε 40,355); $^1$H NMR δ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.01–2.04 (m, 4H, 4-H and 19-CH$_3$), 2.41 (s, 3H, 20-CH$_3$), 6.12–6.46 (m, 5H, vinyls), 7.13 (dd, 1H, 11-H, J=15.1 Hz, J=11.4 Hz), 7.22 (dd, 1H, 5'-H, J=9.1 Hz, J=2.9 Hz), 7.55 (d, 1H, 3'-H, J=2.8 Hz), 8.32 (d, 1H, 6'-H, J=9.1 Hz), 9.05 (s, 1H, X—H), 9.79 (s, 1H, X—H); $^3$C NMR δ 12.87, 13.72, 19.85, 21.91, 29.23, 33.57, 34.84, 40.29, 111.46, 122.61, 123.34, 125.86, 127.54, 128.93, 130.23, 130.88, 131.47, 136.57, 138.43, 138.52, 139.83, 140.23, 151.82, 154.06, 165.60; MS m/e (relative intensity) (M+, 100); HRMS calcd for $C_{26}H_{32}N_2O_4$ (M+Na) 482.1630, found 482.1637

Example 17

N-(3',5'-dibromo-4'-hydroxyphenyl)retinamide (14)

Synthesis was performed as described in Example 1 using 81.7 mg of 4-amino-2,6-dibromophenol. Column chromatography (1:4 EtOAc/hexanes) afforded 81.8 mg (74.5% yield) of yellow solid, decomposed at 130° C. UV-Vis $\lambda_{max}$ 366 nm (ε 53,569); $^1$H NMR δ 1.03 (s, 6H, 16- and 17-CH$_3$), 1.46–1.48 (m, 2H, 2-H), 1.58–1.63 (m, 2H, 3-H), 1.70 (s, 3H, 18-CH$_3$), 2.02–2.05 (m, 4H, 4-H and 19-CH$_3$), 2.41 (s, 3H, 20-CH$_3$), 5.95 (s, 1H, 14-H), 6.15–6.36 (m, 4H, vinyls), 7.09 (dd, 1H, 11-H, J=15.0 Hz, J=11.4 Hz), 7.96 (s, 2H, 2'- and 6'-H), 8.30 (br, 1, X—H), 9.21 (s, 1, X—H); $^{13}$C NMR δ 12.85, 13.61, 19.85, 21.90, 29.23, 33.57, 34.83, 40.30, 111.26, 122.52, 123.69, 128.82, 130.18, 130.87, 131.08, 134.99, 136.68, 138.42, 138.53, 139.58, 147.36, 150.87, 165.62; MS m/e (relative intensity) 572 (M+, 100); HRMS calcd for $C_{26}H_{31}NO_2Br_2$ (M+Na) 572.0609, found 572.0622

Example 18

N-(2'-hydroxy-5'-tert-butylphenyl)retinamide (5)

Synthesis was performed as described in Example 1 using 49.8 mg of 2-amino-4-tert-butylphenol. Column chromatography (3:7 Et$_2$O/hexanes) followed by preparative TLC (3:7 Et$_2$O/hexanes) afforded 68.0 mg (74.7% yield) of yellow solid, m.p. 144–146.5° C. UV-Vis $\lambda_{max}$ 367.5 nm (ε 52,067); $^1$H NMR δ 1.03 (s, 6H, 16- and 17-CH$_3$), 1.25 (s, 9H, Ar—C(CH$_3$)$_3$), 1.46–1.49 (m, 2H, 2-H), 1.59–1.63 (m, 2H, 3-H), 1.71 (s, 3H, 18-CH$_3$), 2.01–2.05 (m, 4H, 4-H and 19-CH$_3$), 2.44 (s, 3H, 20-CH$_3$), 6.17–6.41 (m, 5H, vinyls), 6.83 (d, 1H, 3'-H, J=8.5 Hz), 7.08–7.18 (m, 2H, 11- and 4'-H), 7.33 (d, 1H, 6'-H, J=2.3 Hz), 9.33 (m, 1H, X—H), 9.53 (m, 1H, X—H); $^{13}$C NMR δ 12.90, 13.77, 19.88, 21.93, 29.26, 31.76, 33.60, 34.53, 34.87, 40.33, 118.93, 119.99, 121.50, 123.87, 127.06, 129.03, 130.28, 130.87, 131.60, 136.60, 138.42, 138.55, 139.98, 143.29, 147.64, 151.91, 167.57; MS m/e (relative intensity) 470 (M+, 100); HRMS calcd for $C_{30}H_{41}NO_2$ (M+Na) 470.3035, found 470.3026

Example 19

N-(2'-hydroxy-1'-naphthyl)retinamide (47)

Synthesis was performed as described in Example 1 A using 65.3 mg of 1-amino-2-naphthol hydrochloride and 130 μL of pyridine. Column chromatography (3:2 Et$_2$O/hexanes) afforded 32.8 mg (36.6% yield) of orange solid, m.p. 142.5–143° C. UV-Vis $\lambda_{max}$ 361.0 nm (ε 48,874); $^1$H NMR δ 1.04 (s, 6H, 16- and 17-CH$_3$), 1.47–1.49 (m, 2H, 2-H), 1.59–1.63 (m, 2H, 3-H), 1.72 (s, 3H, 18-CH$_3$), 2.02–2.05 (m, 4H, 4-H and 19-CH$_3$), 2.49 (s, 3H, 20-CH$_3$), 6.19–6.52 (m, 5H, vinyls), 7.16–7.23 (m, 2H, 11- and Ar—H), 7.36 (ddd, 1H, Ar—H, J=J=7.5 Hz, J=0.9 Hz), 7.48 (ddd, 1H, Ar—H, J=J=7.6 Hz, J=1.3 Hz), 7.76 (d, 1H, Ar—H, J=8.9 Hz), 7.84 (d, 1H, Ar—H, J=8.1 Hz), 8.00 (d, 1H, Ar—H, J=8.5 Hz), 9.16 (m, 1H, X—H), 9.63 (m, 1H, X—H); $^{13}$C NMR δ 12.91, 13.87, 19.86, 21.92, 29.25, 33.59, 34.85, 40.31, 118.84, 121.26, 121.85, 124.34, 127.23, 128.69, 128.98, 129.06, 129.94, 130.14, 130.28, 130.87, 131.74, 136.63, 138.41, 138.54, 140.05, 149.92, 152.17, 168.41; MS m/e (relative intensity) 464 (M+, 100); HRMS calcd for $C_{30}H_{35}NO_2$ (M+Na) 464.2565, found 464.2558

Example 20

N-(4$^1$-hydroxy-1'-naphthyl)retinamide (48)

Synthesis was performed as described in Example 1 using 66.0 mg of 4-amino-1-naphthol hydrochloride and 130 μL of pyridine. Column chromatography (1:1 EtOAc/hexanes) followed by crystallization from hexanes/ether afforded 23.0 mg (26.0% yield) of yellow crystals, decomposed at 157° C. UV-Vis $\lambda_{max}$ 359 nm (ε 24,232); $^1$H NMR δ 1.04 (s, 6H, 16- and 17-CH$_3$), 1.47–1.49 (m, 2H, 2-H), 1.59–1.65 (m, 2H, 3-H), 1.71 (s, 3H, 18-CH$_3$), 2.03–2.05 (m, 4H, 4-H and 19-CH$_3$), 2.43 (s, 3H, 20-CH$_3$), 6.17–6.44 (m, 5H, vinyls), 6.89 (d, 1H, Ar—H, J=8.1 Hz), 7.08 (dd, 1H, 11-H, J=15.0 Hz, J=11.5 Hz), 7.44–7.51 (m, 2H, Ar—H), 7.62–7.66 (m, 1H, Ar—H), 8.00 (d, 1H, Ar—H, J=8.3 Hz), 8.24 (d, 1H, Ar—H, J=8.4 Hz), 8.98 (m, 2H, X—H); $^3$C NMR δ 12.85, 13.59, 19.87, 21.92, 29.24, 33.57, 34.85, 40.31, 108.21, 123.13, 123.30, 123.59, 125.38, 125.98, 126.70, 126.86, 128.52, 130.07, 130.35, 131.03, 137.19, 138.53, 139.02, 149.42, 151.69, 166.30; MS m/e (relative intensity) 464 (M+, 100); HRMS calcd for $C_{30}H_{35}NO_2$ (M+Na) 464.2565, found 464.2563

Example 21

N-(3' hydroxymethylphenyl)retinamide (32)

Synthesis was performed as described in Example 1 using 71.9 mg of (i). Preparative TLC (3:8 Et$_2$O/hexanes) afforded 74.1 mg (71.3% yield) of red oil, which was added to a flame-dried 10 mL round bottom flask in ca. 7 mL of dry THF under argon. Tetrabutylammonium fluoride trihydrate (46.8 mg, 1.25 eq) was added and the solution stirred for 1 h. The brown solution was concentrated in vacuuo, reconstituted in ca. 8 mL of EtOAc, washed with water (2×8 mL) and brine (6 mL), and dried over Na$_2$SO$_4$. Column chromatography (3:1 EtOAc/hexanes) afforded 46.4 mg (80.0% yield) of yellow solid, m.p. 118–120.5° C. UV-Vis $\lambda_{max}$ 362 nm (ε 55,943); $^1$H NMR δ 1.03 (s, 6H, 16- and 17-CH$_3$), 1.46–1.49 (m, 2H, 2-H), 1.59–1.65 (m, 2H, 3-H), 1.70 (s, 3H, 18-CH$_3$), 2.01–2.05 (m, 4H, 4-H and 19-CH$_3$), 2.42 (s, 3H, 20-CH$_3$), 4.17 (t, 1H, O—H, J=5.8 Hz), 4.59 (d, 2H, Ar—CH$_2$, J=6.0 Hz), 6.03 (s, 1H, 14-H), 6.15–6.37 (m, 4H, vinyls), 7.01–7.11 (m, 2H, 11- and Ar—H), 7.23 (dd, 1H, 5'-H, J=J=7.8 Hz), 7.60 (d, 1H, Ar—H, J=7.9 Hz), 7.71 (s, 1H, 2'-H), 9.15 (br, 1H, CON—H); $^3$C NMR δ 12.85, 13.55, 19.87, 21.91, 29.24, 33.58, 34.85, 40.31, 64.65, 118.11, 118.41, 122.10, 123.41, 128.66, 129.22, 130.13, 130.64, 130.95, 136.97, 138.48, 138.57, 139.27, 140.63, 144.08, 150.02, 165.68; MS m/e (relative intensity) 428 (M+, 100); HRMS calcd for $C_{27}H_{35}NO_2$ (M+Na) 428.2564, found 428.2567

Example 22

N-(3'-hydroxy-2-naphthyl)retinamide (50)

Synthesis was performed as described in Example 1 using 48.9 mg of 3-amino-2-naphthol. Column chromatography (1:3 EtOAc/hexanes) afforded 77.9 mg (88.2% yield) of yellow solid, m.p. 187–188.5° C. UV-Vis $\lambda_{max}$ 370 nm (ε 57,004); $^1$H NMR δ 1.03 (s, 6H, 16- and 17-CH$_3$), 1.46–1.49 (m, 2H, 2-H), 1.59–1.63 (m, 2H, 3-H), 1.71 (s, 3H, 18-CH$_3$), 2.01–2.05 (m, 4H, 4-H and 19-CH$_3$), 2.47 (s, 3H, 20-CH$_3$), 6.17–6.44 (m, 5H, vinyls), 7.14 (dd, 1H, 11-H, J=15.1 Hz, J=11.4 Hz), 7.25–7.32 (m, 3H, 5'-, 6'- and Ar—H), 7.62 (d, 1H, Ar—H, J=7.8 Hz), 7.73 (d, 1H, Ar—H, J=7.7 Hz), 8.53 (s, 1H, Ar—H), 9.02 (s, 1H, X—H), 9.70 (br, 1H, X—H);

$^{13}$C NMR δ 12.88, 13.72, 19.87, 21.92, 29.24, 33.59, 34.85, 40.31, 110.97, 118.36, 122.57, 124.40, 125.79, 126.55, 128.05, 128.87, 129.65, 129.73, 130.20, 130.92, 131.23, 132.23, 136.79, 138.46, 138.56, 139.71, 147.64, 151.35, 166.76; MS m/e (relative intensity) 464 (M$^+$, 100); HRMS calcd for $C_{30}H_{35}NO_2$ (M+Na) 464.2565, found 464.2558

Example 23

N-(2'-hydroxymethylphenyl)retinamide (31)

Synthesis was performed as described in Example 1 using 93.0 mg of (ii). Preparative TLC (3:7 $Et_2O$/hexanes) afforded 88.9 mg of crude product, which was added to a flame-dried 10 mL round bottom flask in ca. 7 mL of dry THF under argon. Tetrabutylammonium fluoride trihydrate (64.2 mg, 1.44 eq) was added and the solution stirred for 0.5 h. Column chromatography (2:3 EtOAc/hexanes) afforded 46.3 mg (57.1% yield, 2 steps) of yellow solid, m.p. 72–74° C. $^1$H NMR δ 1.03 (s, 6H, 16- and 17-$CH_3$), 1.46–1.49 (m, 2H, 2-H), 1.59–1.65 (m, 2H, 3-H), 1.71 (s, 3H, 18-$CH_3$), 2.01–2.04 (m, 4H, 4-H and 19-$CH_3$), 2.41 (s, 3H, 20-$CH_3$), 4.68 (s, 3H, Ar—$CH_2$ and O—H), 6.02 (s, 1H, 14-H), 6.16–6.44 (m, 4H, vinyls), 7.03–7.12 (m, 2H, 11- and Ar—H), 7.23–7.27 (m, 2H, Ar—H), 8.09 (d, 1H, Ar—H, J=7.1 Hz), 9.11 (br, 1H, CON—H); $^{13}$C NMR δ 12.86, 13.58, 19.87, 21.91, 29.24, 33.57, 34.85, 40.30, 63.63, 122.76, 123.39, 124.44, 128.59, 128.69, 129.10, 130.12, 130.79, 130.95, 132.16, 136.85, 138.48, 138.55, 138.72, 139.33, 150.19, 165.65; MS m/e (relative intensity) 428 (M$^+$, 100); HRMS calcd for $C_{27}H_{35}NO_2$ (M+Na) 428.2565, found 428.2553

Example 24

N-(5'-hydroxy-1'-naphthyl) retinamide (49)

Synthesis was performed as described in Example 1 using 47.8 mg of 5-amino-1-naphthol. Column chromatography (2:3 EtOAc/hexanes) followed by preparative TLC (35:65 EtOAc/$Et_2O$) afforded 37.9 mg (42.9% yield) of orange waxy solid. UV-Vis $λ_{max}$ 360.5 nm (ε 36,882); $^1$H NMR δ 1.04 (s, 6H, 16- and 17-$CH_3$), 1.46–1.49 (in, 2H, 2-H), 1.59–1.65 (m, 2H, 3-H), 1.71 (s, 3H, 18-$CH_3$), 2.01–2.03 (m, 4H, 4-H and 19-$CH_3$), 2.45 (s, 3H, 20-$CH_3$), 6.17–6.42 (m, 5H, vinyls), 6.92 (d, 1H, Ar—H, J=7.4 Hz), 7.10 (dd, 1H, 11-H, J=14.9 Hz, J=11.4 Hz), 7.29 (dd, 1H, Ar—H, J=J=8.0 Hz), 7.42 (dd, 1H, Ar—H, J=J=8.0 Hz), 7.62 (d, 1H, Ar—H, J=8.6 Hz), 8.05–8.08 (m, 2H, Ar—H), 9.07 (m, 2H, X—H); $^{13}$C NMR δ 12.90, 13.73, 19.90, 21.96, 29.28, 33.60, 34.88, 40.33, 109.02, 113.88, 119.73, 121.51, 123.44, 124.98, 126.54, 128.66, 129.06, 129.64, 130.13, 130.63, 131.02, 134.51, 137.08, 138.52, 138.58, 139.25, 150.10, 154.33, 166.22; MS m/e (relative intensity) (M$^+$, 100); HRMS calcd for $C_{30}H_{35}NO_2$ (M+Na) 464.2565, found 464.2548

Example 25

N-(2'-hydroxy-5'-nitrophenyl)retinamide (19)

Synthesis was performed as described in Example 1 using 46.5 mg of 2-amino-4-nitrophenol. Preparative TLC (1:3 EtOAc/hexanes, then 1:1 EtOAc/hexanes) afforded 17.1 mg (19.6% yield) of yellow solid, m.p. 151.5–153° C. UV-Vis max 371.5 nm; $^1$H NMR δ 1.03 (s, 6H, 16- and 17-$CH_3$), 1.46–1.49 (m, 2H, 2-H), 1.58–1.65 (m, 2H, 3-H), 1.71 (s, 3H, 18-$CH_3$), 2.01–2.04 (m, 4H, 4-H and 19-$CH_3$), 2.45 (s, 3H, 20-$CH_3$), 6.17–6.42 (m, 5H, vinyls), 7.06 (d, 1H, 3'-H, J=8.9 Hz), 7.17 (dd, 1H, 11-H, J=15.0 Hz, J=11.4 Hz), 7.91 (dd, 1H, 4'-H, J=8.9 Hz, J=2.8 Hz), 8.87 (d, 1H, 6'-H, J=2.7 Hz), 9.17 (s, 1H, X—H), 10.84 (br, 1H, X—H); $^{13}$C NMR δ 12.88, 13.14, 19.84, 21.90, 29.22, 33.57, 34.84, 40.29, 117.07, 117.36, 121.37, 121.47, 127.56, 128.49, 130.30, 130.82, 131.89, 136.46, 138.38, 138.52, 140.19, 141.37, 152.72, 154.25, 167.30; MS m/e (relative intensity) (M$^+$, 100); HRMS calcd for $C_{26}H_{32}N_2O_4$ (M+Na) 459.2260, found 459.2236

Example 26

N-(2'-hydroxy-4'-nitrophenyl)retinamide (18)

Synthesis was performed as described in Example 1 using 47.2 mg of 2-amino-5-nitrophenol. Column chromatography (1:3 EtOAc/hexanes) followed by preparative TLC (1:5 EtOAc/hexanes) afforded 24.7 mg (28.3% yield) of orange solid, m.p. 152–153.5° C. UV-Vis $λ_{max}$ 391 nm (ε 39,167); $^1$H NMR δ 1.03 (s, 6H, 16- and 17-$CH_3$), 1.46–1.49 (m, 2H, 2-H), 1.58–1.65 (m, 2H, 3-H), 1.71 (s, 3H, 18-$CH_3$), 2.01–2.05 (m, 4H, 4-H and 19-$CH_3$), 2.45 (s, 3H, 20-$CH_3$), 6.17–6.42 (m, 5H, vinyls), 7.18 (dd, 1H, 11-H, J=15.0 Hz, J=11.4 Hz), 7.73 (d, 1H, 3'-H, J=2.5 Hz), 7.77 (dd, 1H, 5'-H, J=8.9 Hz, J=2.6 Hz), 8.23 (d, 1H, 6'-H, J=2.7 Hz), 9.19 (s, 1H, X—H); $^{13}$C NMR δ 12.89, 13.86, 19.85, 21.91, 29.23, 33.59, 34.85, 40.31, 111.52, 116.53, 120.78, 121.69, 129.18, 130.33, 130.82, 132.00, 134.88, 136.47, 138.39, 138.54, 140.28, 144.41, 147.79, 152.98, 167.01; MS m/e (relative intensity) (M$^+$, 100); HRMS calcd for $C_{26}H_{32}N_2O_4$ (M+Na) 459.2260, found 459.2248

Example 27

N-(4'-hydroxy-3'-nitrophenyl)retinamide (17)

Synthesis was performed as described in Example 1 using 47.2 mg of 4-amino-2-nitrophenol. Column chromatography (1:3 EtOAc/hexanes) afforded 64.7 mg (74.1% yield) of yellow solid, m.p. 157–159.5° C. UV-Vis $λ_{max}$ 365.5 nm (ε 56,317); $^1$H NMR δ 1.03 (s, 6H, 16- and 17-$CH_3$), 1.46–1.49 (m, 2H, 2-H), 1.59–1.65 (m, 2H, 3-H), 1.71 (s, 3H, 18-$CH_3$), 2.01–2.05 (m, 4H, 4-H and 19-$CH_3$), 2.43 (s, 3H, 20-$CH_3$), 5.99 (s, 1H, 14-H), 6.15–6.38 (m, 4H, vinyls), 7.08–7.16 (m, 2H, 11- and 5'-H), 7.85 (dd, 1H, 6'-H, J=9.0 Hz, J=2.6 Hz), 8.74 (d, 1H, 2'-H, J=2.4 Hz), 9.40 (s, 1H, X—H), 10.25 (br, 1H, X—H); $^{13}$C NMR δ 12.85, 13.63, 19.86, 21.90, 29.23, 33.58, 34.85, 40.31, 114.82, 120.69, 122.43, 128.86, 129.95, 130.20, 130.86, 131.17, 133.48, 134.58, 136.67, 138.42, 138.54, 139.65, 151.07, 151.27, 165.83; MS m/e (relative intensity) (M$^+$, 100); HRMS calcd for $C_{26}H_{32}N_2O_4$ (M+Na) 459.2260, found 459.2235

Example 28

N-(2'-hydroxy-3'-carboxymethylphenyl)retinamide (20)

Synthesis was performed as described in Example 1 using 2 mL of 55.4 g 164-A2/2.2 mL THF. Column chromatography (3:7 $Et_2O$/hexanes) afforded 57.3 mg (63.7% yield) of orange solid. UV-Vis $λ_{max}$ 365.5 nm (ε 57,202); $^1$H NMR δ 1.03 (s, 6H, 16- and 17-$CH_3$), 1.45–1.48 (m, 2H, 2-H), 1.58–1.64 (m, 2H, 3-H), 1.71 (s, 3H, 18-$CH_3$), 2.02–2.05 (m, 4H, 4-H and 19-$CH_3$), 2.43 (s, 3H, 20-$CH_3$), 3.96 (s, 3H, —$CO_2CH_3$), 6.16–6.40 (m, 5H, vinyls), 6.91 (dd, 1H, 5'-H, J=8.1 Hz, J=8.0 Hz), 7.09 (dd, 1H, 11-H, J=15.0 Hz, J=11.4 Hz), 7.51 (dd, 1H, Ar—H, J=8.1 Hz, J=1.5 Hz), 8.51 (s, 1H, X—H), 8.64 (d, 1H, Ar—H, J=7.9 Hz), 11.27 (s, 1H, X—H);

$^{13}$C NMR δ 12.87, 13.64, 19.86, 21.93, 29.25, 33.58, 34.83, 40.29, 53.04, 112.55, 119.68, 122.98, 124.08, 126.18, 128.71, 129.17, 130.14, 130.88, 130.93, 136.86, 138.46, 138.52, 139.43, 150.79, 151.62, 165.77, 171.62

Example 29

N-(2'-hydroxy-3'-carboxyphenyl)retinamide (21)

Potassium hydroxide (4.0 mL of 5N) was added to a solution of 56.0 mg of 29P in methanol/THF (ca. 7 mL) and the red mixture stirred for 48 h. Aqueous workup with 1N HCl followed by preparative TLC (4:1 EtOAc/CH$_3$OH) afforded 41.8 mg (76.8% yield) of yellow solid, m.p. 175° C. UV-Vis λ$_{max}$ 365 nm (ε 39,316); $^1$H NMR δ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.02–2.05 (m, 4H, 4-H and 19-CH$_3$), 2.42 (s, 3H, 20-CH$_3$), 6.17–6.32 (m, 4H, vinyls), 6.43 (d, 1H, 12-H, J=15.1 Hz), 6.58 (1H, 5'-H, J=J 7.8 Hz), 7.07 (dd, 1H, 11-H, J=15.0 Hz, J=11.4 Hz), 7.53 (d, 1H, Ar—H, J=7.0 Hz), 8.33 (br, 1H, X—H), 8.40 (d, 1H, Ar—H, J=7.5 Hz); $^{13}$C NMR δ 12.84, 13.47, 19.87, 21.91, 29.23, 33.57, 34.85, 40.31, 115.95, 119.26, 121.92, 123.88, 125.16, 127.61, 128.47, 130.05, 130.29, 131.06, 137.20, 138.57, 139.01, 149.46, 154.14, 165.31,

Example 30

N-(2'-hydroxy-6'-carboxymethyphenyl)retinamide (23)

Synthesis was performed as described in Example 1 using 47.9 mg of 164-B. Column chromatography (1:4 Et$_2$O/hexanes) afforded 50.0 mg (58.9% yield) of orange solid. UV-Vis λ$_{max}$ 371.5 nm (ε 38,272); $^1$H NMR δ 1.04 (s, 6H, 16- and 17-CH$_3$), 1.46–1.49 (m, 2H, 2-H), 1.59–1.65 (m, 2H, 3-H), 1.71 (s, 3H, 18-CH$_3$), 2.02–2.05 (m, 4H, 4-H and 19-CH$_3$), 2.45 (s, 3H, 20-CH$_3$), 3.92 (s, 3H, —CO$_2$CH$_3$), 6.19–6.37 (m, 4H, vinyls), 6.54 (d, 1H, 12-H, J=15.0 Hz), 7.17–7.25 (m, 3H, 11- and Ar—H), 7.58 (dd, 1H, Ar—H, J=6.5 Hz, J=2.8 Hz), 10.16–10.17 (m, 1H, X—H), 11.00–11.02 (m, 1H, X—H); $^{13}$C NMR δ 12.92, 13.87, 19.85, 21.92, 29.24, 33.59, 34.86, 40.31, 53.04, 120.87, 121.17, 123.36, 125.54, 126.55, 129.37, 129.67, 130.40, 130.83, 132.60, 136.26, 138.39, 138.53, 140.64, 151.40, 153.99, 168.43, 169.27

Example 31

N-(2'-hydroxy-6'-carboxyphenyl)retinamide (24)

Potassium hydroxide (2.8 mL of 5N) was added to a solution of 50.7 mg of 30P in methanol/THF (ca. 7 mL) and the yellow mixture stirred for 48 h. Aqueous workup with 1N HCl followed by preparative TLC (10:1 EtOAc/hexanes) afforded 13.7 mg (35.9% yield) of yellow solid, m.p. 149–150° C. UV-Vis λ$_{max}$ 374.5 nm (ε 38,085); $^1$H NMR δ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.02–2.05 (m, 4H, 4-H and 19-CH$_3$), 2.41 (s, 3H, 20-CH$_3$), 6.15–6.19 (m, 3H, 8-, 10-, and 14-H), 6.32 (d, 1H, 7-H, J=16.2 Hz), 6.43 (d, 1H, 12-H, J=15.1 Hz), 7.07–7.17 (m, 1H, 11- and Ar—H), 7.69 (dd, 1H, Ar—H, J=7.0 Hz, J=1.5 Hz); $^{13}$C NMR δ 12.89, 13.77, 19.86, 21.96, 29.25, 33.59, 34.85, 40.30, 121.53, 122.88, 123.82, 124.65, 125.97, 129.06, 130.17, 130.30, 130.94, 132.12, 136.46, 138.47, 138.60, 140.21, 150.97, 153.22, 168.19, 171.86

Example 32

N-(3'-hydroxy-4'-carboxymethylphenyl)retinamide (25)

Synthesis was performed as described in Example 1 using 2 mL of 79.6 mg 164-D2/3.2 mL THF. Column chromatography (1:3 EtOAc/hexanes) afforded 55.7 mg (61.3% yield) of yellow solid. UV-Vis λ$_{max}$ 371 nm (ε 57,416); $^1$H NMR δ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.01–2.05 (m, 4H, 4-H and 19-CH$_3$), 2.42 (s, 3H, 20-CH$_3$), 3.92 (s, 3H, —CO$_2$CH$_3$), 6.01 (s, 1H, 14-H), 6.16–6.37 (m, 4H, vinyls), 7.09–7.18 (m, 2H, 11- and 6'-H), 7.54 (d, 1H, 2'-H, J=1.8 Hz), 7.74 (d, 1H, 5'-H, J=8.8 Hz), 9.44 (s, 1H, X—H), 10.82 (s, 1H, X—H); $^{13}$C NMR δ 12.86, 13.69, 19.67, 21.90, 29.23, 33.58, 34.85, 40.31, 52.53, 106.85, 107.80, 111.15, 122.52, 128.96, 130.25, 130.85, 131.34, 131.45, 136.61, 138.41, 138.54, 139.84, 147.35, 151.70, 163.50, 166.10, 170.99

Example 33

N-(3'-hydroxy-4'-carboxyphenyl)retinamide (26)

Potassium hydroxide (3.5 mL of 5N) was added to a solution of 52.8 mg of 31P in methanol/THF (ca. 6.5 mL) and the yellow mixture stirred for 48 h. Aqueous workup with 1N HCl followed by preparative TLC (4:1 EtOAc/CH$_3$OH) afforded 31.2 mg (61.0% yield) of yellow waxy solid. UV-Vis λ$_{max}$ 367 nm (ε 47,995); $^1$H NMR δ 1.02 (s, 6H, 16- and 17-CH$_3$), 1.45–1.48 (m, 2H, 2-H), 1.60–1.63 (m, 2H, 3-H), 1.70 (s, 3H, 18-CH$_3$), 2.00–2.05 (m, 4H, 4-H and 19-CH$_3$), 2.38 (s, 3H, 20-CH$_3$), 6.02 (s, 1H, 14-H), 6.14–6.34 (m, 4H, vinyls), 6.79 (br, 1H, Ar—H), 7.03 (dd, 1H, 11-H, J=11.4 Hz, J=15.0 Hz), 7.39 (br, 1H, Ar—H), 7.92 (br, 1H), 9.16 (br, 1H,); $^{13}$C NMR δ 12.86, 13.64, 19.86, 21.95, 29.22, 33.58, 34.83, 40.29, 106.69, 109.85, 114.38, 123.46, 128.56, 130.09, 130.64, 131.00, 133.18, 136.61, 138.49, 138.53, 139.19, 144.63, 150.28, 163.44, 165.85

Example 34

N-methyl-(4'-hydroxyphenyl)retinamide (46)

Synthesis was performed as described in Example 1 A using 52.7 mg of 4-(methylamino)phenol sulfate. Column chromatography (1:3 EtOAc/hexanes) afforded 55.3 mg (68.2% yield) of yellow solid, m.p. 190–191° C. UV-Vis λmax 355.5 nm (ε 44,201); $^1$H NMR δ 1.00 (s, 6H, 16- and 17-CH$_3$), 1.44–1.47 (m, 2H, 2-H), 1.57–1.63 (m, 2H, 3-H), 1.67 (s, 3H, 18-CH$_3$), 1.96–2.05 (m, 4H, 4-H and 19-CH$_3$), 2.25 (s, 3H, 20-CH$_3$), 3.19 (s, 3H, N—CH$_3$), 5.63 (s, 1H, 14-H), 6.06–6.27 (m, 4H, vinyls), 6.85–6.90 (m, 3H, 11- and 3'-H), 7.05–7.07 (m, 2H, 2'-H), 8.58 (s, 1H, —OH); $^{13}$C NMR δ 12.75, 13.77, 19.85, 21.87, 29.22, 33.53, 34.82, 37.06, 40.28, 116.77, 122.91, 128.18, 129.19, 129.50, 129.92, 131.04, 137.07, 137.24, 138.47, 138.59, 147.01, 157.31, 167.23

Example 35

N-(2'-hydroxy-5'-carboxymethylphenyl)retinamide (29)

Synthesis was performed as described in Example 1 using 2 mL of 71.6 mg 164-C2/2.8 mL THF. Column chromatography (1:2 EtOAc/hexanes) afforded 77.0 mg (85.6% yield) of yellow solid. UV-Vis λ$_{max}$ 373 nm (ε 46,589); $^1$H NMR δ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.01–2.04 (m, 4H, 4-H and 19-CH$_3$), 2.44 (s, 3H, 20-CH$_3$), 3.84 (s, 3H, —CO$_2$CH$_3$), 6.17–6.42 (m, 5H, vinyls), 7.16 (dd, 1H, 11-H, J=15.0 Hz, J=11.4 Hz), 7.49–7.53 (m, 2H, Ar—H), 7.85–7.89 (m, 1H, Ar—H), 9.20–9.22 (m, 1H, X—H), 9.79 (br, 1H, X—H); $^{13}$C NMR δ 12.87, 13.78, 19.84, 21.89, 29.22, 33.57, 34.84, 40.29, 52.11, 118.36, 121.44, 121.69, 122.21, 127.19, 129.06, 130.28, 130.83, 131.74, 132.44, 136.53, 138.40, 138.53, 140.08, 147.91, 152.40, 166.73, 167.07

Example 36

N-(2'-hydroxy-4'-carboxyphenyl)retinamide (22)

Potassium hydroxide (2.0 mL of 5N) was added to a solution of 62.1 mg of 34P in methanol/THF (ca. 6 mL) and the mixture stirred for 24 h. Aqueous workup with 1N HCl followed by preparative TLC (EtOAc) afforded 72.0 mg (>100% yield) of yellow solid, m.p. 185° C. UV-Vis $\lambda_{max}$ 371.5 nm ($\epsilon$ 37,990); $^1$H NMR $\delta$ 1.03 (s, 6H, 16- and 17-CH$_3$), 1.46–1.49 (m, 2H, 2-H), 1.59–1.65 (m, 2H, 3-H), 1.71 (s, 3H, 18-CH$_3$), 2.01–2.05 (m, 4H, 4-H and 19-CH$_3$), 2.44 (s, 3H, 20-CH$_3$), 6.17–6.42 (m, 5H, vinyls), 7.16 (dd, 1H, 11-H, J=15.0 Hz, J=11.4 Hz), 7.52 (dd, 1H, 5'-H, J=8.4 Hz, J=1.8 Hz), 7.58 (d, 1H, 3'-H), 7.85 (d, 1H, 6'-H, J=1.7 Hz), 9.26 (s, 1H, X—H); $^{13}$C NMR $\delta$ 12.88, 13.78, 19.86, 21.91, 29.23, 33.58, 34.85, 40.31, 118.94, 121.47, 121.84, 122.42, 128.17, 129.04, 130.28, 130.87, 131.69, 132.31, 136.60, 138.43, 138.54, 140.03, 148.19, 152.27, 167.17, 167.56

Example 37

N-(4'-hydroxy-3'-carboxymethylphenyl)retinamide (27)

Synthesis was performed as described in Example 1 using 39.1 mg of 164-F2. Column chromatography (1:3 EtOAc/hexanes) afforded 66.1 mg (81.0% yield) of yellow solid. UV-Vis $\lambda_{max}$ 362.5 nm ($\epsilon$ 53,554); $^1$H NMR $\delta$ 1.03 (s, 6H, 16- and 17-CH$_3$), 1.46–1.49 (m, 2H, 2-H), 1.59–1.65 (m, 2H, 3-H), 1.70 (s, 3H, 18-CH$_3$), 2.02–2.05 (m, 4H, 4-H and 19-CH$_3$), 2.42 (s, 3H, 20-CH$_3$), 3.96 (s, 3H, —CO$_2$CH$_3$), 6.00 (s, 1H, 14-H), 6.15–6.37 (m, 4H, vinyls), 6.90 (d, 1H, 5'-H, J=9.0 Hz), 7.08 (dd, 1H, 11-H, J=15.0 Hz, J=11.4 Hz), 7.75 (dd, 1H, 6'-H, J=8.9 Hz, J=2.5 Hz), 8.36 (d, 1H, 2'-H, J=2.5 Hz), 9.18 (s, 1H, X—H), 10.51 (s, 1H, X—H); $^{13}$C NMR $\delta$ 12.84, 13.55, 19.85, 21.90, 29.23, 33.57, 34.84, 40.29, 52.86, 112.59, 118.19, 120.74, 123.02, 128.52, 128.68, 130.13, 130.72, 130.92, 132.62, 136.87, 138.45, 138.54, 139.32, 150.15, 158.35, 165.56, 171.22

Example 38

N-(4'-hydroxy-3'-carboxyphenyl)retinamide (28)

Potassium hydroxide (3.0 mL of 5N) was added to a solution of 47.1 mg of $^{35}$P in methanol/THF (ca. 7 mL) and the mixture stirred for 48 h. Aqueous workup with 1N HCl followed by preparative TLC (4:1 EtOAc/hexanes) afforded 79.4 mg (75.8% yield) of yellow solid, m.p. 185° C. UV-Vis $\lambda_{max}$ 361 nm ($\epsilon$ 28,467); $^1$H NMR $\delta$ 1.04 (s, 6H, 16- and 17-CH$_3$), 1.46–1.49 (m, 2H, 2-H), 1.59–1.65 (m, 2H, 3-H), 1.72 (s, 3H, 18-CH$_3$), 2.03–2.05 (m, 4H, 4-H and 19-CH$_3$), 2.34 (s, 3H, 20-CH$_3$), 5.99 (s, 1H, 14-H), 6.16–6.37 (m, 4H, vinyls), 6.62 (br, 1H, Ar—H), 6.96 (m, 1H, 11-H), 7.85 (br, 1H, Ar—H), 8.10 (br, 1H, Ar—H), 8.93 (br, 1H, X—H); $^{13}$C NMR $\delta$ 12.89, 13.59, 19.91, 22.03, 29.22, 33.60, 34.85, 40.30, 116.56, 119.10, 123.66, 123.96, 126.29, 128.23, 129.95, 130.04, 130.82, 131.26, 137.05, 138.57, 138.66, 149.07, 158.78, 165.58, 176.51.

Example 39

N-(4'-aminophenyl)retinamide (33)

Synthesis was performed as described in General Procedure A using 30.0 mg of iii, 35.9 mg of atRA, 131.0 mg of resin-bound triphenylphosphine, 9.6 $\mu$L of HCA, and 60 $\mu$L of pyridine. The heterogeneous mixture was filtered, concentrated, reconstituted in 20 mL EtOAc, and extracted twice with 20 mL of 1N HCl. The resulting N-(4'-trifluoroacetamidopheny) retinamide was hydrolyzed with 2.0 mL of 5N KOH in ca. 6 mL of MeOH/THF, with stirring over 20 h. Aqueous workup, followed by preparative TLC (7:5 (EtOAc/hexanes) afforded 35.6 mg (76.2% yield) of red oil. UV-Vis $\lambda_{max}$ 364.5 nm ($\epsilon$ 43,925); $^1$H NMR $\delta$ 1.03 (s, 6H, 16- and 17-CH$_3$), 1.45–1.48 (m, 2H, 2-H), 1.58–1.64 (m, 2H, 3-H), 1.71 (s, 3H, 18-CH$_3$), 2.01–2.05 (m, 4H, 4-H and 19-CH$_3$), 2.40 (s, 3H, 20-CH$_3$), 4.48 (br, 2H, —NH$_2$), 5.98 (s, 1H, 14-H), 6.14–6.34 (m, 4H, vinyls), 6.59 (d, 2H, J=8.7 Hz), 7.02 (s, 1H, 1-H, J=15.0 Hz, J=11.4 Hz), 7.42 (d, 2H, J=8.7 Hz), 8.88 (s, 1H, CO—NH); $^{13}$C NMR $\delta$ 12.61, 13.42, 19.85, 21.90, 29.23, 33.55, 34.81, 40.27, 115.09, 120.45, 120.60, 121.49, 123.97, 128.55, 130.42, 130.73, 131.01, 137.21, 138.49, 138.79, 139.10, 148.69, 165.00

Example 40

N-(4'-Acetamidophenyl)retinamide (34)

Synthesis was performed as described in Example 1 using 4-acetamidoaniline. $^1$H NMR (DMSO-d$_6$) $\delta$ 1.02 (s, 6H), 1.44–1.45 (m, 2H), 1.58 (m, 2H), 1.69 (s, 3H) 1.98–2.08 (m, 8H), 2.34 (s, 3H), s (6.00, 1H), 6.15–6.38 (m, 4H), 6.99 (dd, 1H, J=15.9 Hz, J=11.8 Hz), 7.48 (d, 2H, J=8.9 Hz), 7.55 (d, 2H, J=8.9 Hz), 9.85 (s, 11H), 9.94 (s, 1H); $^{13}$C NMR (DMSO-d$_6$) $\delta$ 12.45, 13.14, 18.60, 21.36, 23.72, 28.68, 32.48, 33.73, 119.23, 122.60, 127.33, 129.22, 129.95, 134.54, 134.66, 135.89, 136.83, 137.17, 138.02, 147.88, 164.35, 167.73; HRMS (ES) calcd for C$_{28}$H$_{36}$N$_2$O$_2$Na (M+Na) 455.2674, found 455.2689.

Example 41

N-(4'-Trifluoroacetamidophenyl)retinamide (35)
Reactant 4 trifluoracetamidoaniline Trifluoroaceticanhydride (120 $\mu$L, 0.850 mmol) was added dropwise to a solution of phenylenediamine (0.1057 g, 0.977 mmol) in 2.0 mL of pyridine at 0° C. under an argon atmosphere. The red solution was stirred for an hour, then subjected to aqueous workup. Preparative TLC (2:1 EtOAc/hexanes) afforded 21.3 mg of crude product having a $^1$H NMR spectrum consistent with the structure of the desired product. $^1$H NMR $\epsilon$ XXX (br, 2H, —NH$_2$), 6.66 (d, 2H, J=8.77 Hz), 7.38 (d, 2H, J=8.78 Hz), 9.89 (br, 1H, CO—NH).

Synthesis was performed as described in Example 1 using 4-trifluoroacetamidoaniline. $^1$H NMR (acetone-d$_6$) $\delta$ 1.00 (s, 6H), 1.43–1.46 (m, 2H), 1.56–1.61 (m, 2H), 1.68 (s, 3H), 1.98–2.03 (m, 5H), 2.39 (s, 3H), 6.00 (s, 1H), 6.13–6.35 (m, 4H), 7.06 (dd, 1H, J=15.9 Hz, J=11.3 Hz), 7.62 (d, 2H, J=8.9 Hz), 7.73 (d, 2H, J=8.9 Hz), 9.29 (s, 1H), 10.19 (s, 1H); $^{13}$C NMR (acetone-d$_6$) $\delta$ 12.79, 13.56, 19.83, 21.82, 33.54, 34.82, 40.32, 120.25, 122.10, 123.04, 128.71, 130.12, 130.74, 130.83, 132.40, 136.81, 138.40, 138.55, 139.35, 150.32, 165.67; HRMS (ES) calcd for C$_{28}$H$_{33}$F$_3$N$_2$O$_2$Na (M+Na) 509.2392, found 509.2408.

Example 42

N-(4'-Azidophenyl)retinamide (36)

Synthesis was performed as described in Example 1 using 4-azidoaniline hydrochloride. $^1$H NMR (acetone-d$_6$) $\delta$ 1.06 (s, 6H), 1.49–1.52 (m, 2H), 1.63–1.65 (m, 2H), 1.73 (s, 3H), 2.11 (m, 5H), 2.45 (d, 3H, J=0.9 Hz), 6.03 (s, 1H), 6.18–6.43

(m, 4H), 7.03–7.15 (m, 3H), 7.81 (d, 2H, J=8.1 Hz), 9.31 (s, 1H); $^{13}$C NMR (acetone-d$_6$) δ 12.87, 13.63, 19.91, 21.90, 33.62, 34.89, 40.39, 120.09, 121.39, 123.03, 128.78, 130.19, 130.82, 130.91, 135.18, 136.87, 138.01, 138.46, 138.61, 139.42, 150.39, 165.59; HRMS (ES) calcd for C$_{26}$H$_{32}$N$_4$ONa (M+Na) 439.2474, found 439.2470.

Example 43

N-(2'-Hydroxy-4'-azidophenyl)retinamide (37)

Synthesis was performed as described in Example 1 using 2-amino-5-azidophenol hydrochloride. $^1$H NMR (acetone-d$_6$) δ 1.01 (s, 6H), 1.44–1.47 (m, 2H), 1.57–1.63 (m, 2H), 1.69 (s, 3H), 2.02 (m, 5H), 2.41 (d, 3H, J=0.7 Hz), 6.15–6.39 (m, 5H), 6.53–6.6.58 (m, 2H), 7.13 (dd, 1H, J=15.5 Hz, J=11.7 Hz), 7.44 (d, 1H, J=8.4 Hz), 9.32 (s, 1H); $^{13}$C NMR (acetone-d$_6$) δ 12.73, 13.62, 19.71, 21.77, 33.44, 34.70, 40.16, 109.14, 110.98, 121.20, 123.90, 125.26, 128.90, 130.14, 130.69, 131.53, 136.40, 137.93, 138.25, 138.39, 139.90, 150.79, 152.00, 167.29; HRMS (ES) calcd for C$_{26}$H$_{32}$N$_4$O$_2$Na (M+Na) 455.2423, found 455.2414.

Example 44

N-(4'-Isothiocyanatophenyl)retinamide (38)

A dry, argon flushed 3-neck round bottom flask equipped with a magnetic stir bar was charged with resin-bound triphenylphosphine (240 mg, 0.72 mmol) and CH$_2$Cl$_2$ (5 mL) and cooled to 0° C. To this stirred suspension was added via cannula a CH$_2$Cl$_2$ solution of N-(4'-azidophenyl)retinamide (98 mg, 0.24 mmol). The reaction mixture was stirred at 0° C. for 1 h, after which, CS$_2$ (0.03 mL, 0.50 mmol) was added via a syringe. The stirred suspension was maintained under an argon atmosphere and was allowed to warm to room temperature overnight. The contents of the reaction mixture were filtered, concentrated, and chromatographed on silica gel (20% ether/hexanes) to yield 56 mg of a yellow solid (55%). $^1$H NMR (acetone-d$_6$) δ 1.04 (s, 6H), 1.47–1.50 (m, 2H), 1.61–1.64 (m, 2H), 1.71 (s, 3H), 2.04 (m, 5H), 2.43 (d, 3H, J=0.8 Hz), 6.02 (s, 1H), 6.16–6.38 (m, 4H), 7.12 (dd, 1H, J=15.9 Hz, J=11.3 Hz), 7.32 (d, 2H, J=8.9 Hz), 7.81 (d, 2H, J=8.9 Hz), 9.43 (s, 11H); $^{13}$C NMR (acetone-d$_6$) δ 12.88, 13.69, 19.91, 21.90, 33.62, 34.89, 40.39, 120.84, 122.72, 125.98, 127.05, 128.91, 130.24, 130.86, 131.15, 136.72, 138.43, 138.61, 139.66, 140.30, 151.06, 165.74, 165.82; HRMS (ES) calcd for C$_{27}$H$_{32}$N$_2$OSNa (M+Na) 455.2133, found 455.2130.

Example 45

N-(4'-Chloroacetamidophenyl)retinamide (39)

A dry, argon flushed round bottom flask equipped with a magnetic stir bar was charged with N-(4'-aminophenyl)retinamide (25 mg, 0.064 mmol) and THF (2 mL) and cooled to 0° C. To this stirred solution was added chloroacetyl chloride (10.9 mg, 0.096 mmol). The solution was stirred at 0° C. for 1.5 h, then diluted with water and extracted with ethyl acetate. The product was purified using preparative TLC (50% ethyl acetate/hexanes).

$^1$H NMR (acetone-d$_6$) δ 1.01 (s, 6H), 1.44–1.47 (m, 2H), 1.58–1.60 (m, 2H), 1.68 (s, 3H), 2.01 (m, 5H), 2.40 (s, 3H), 4.20 (s, 2H), 6.00 (s, 1H), 6.14–6.35 (m, 4H), 7.05 (dd, 1H, J=15.9 Hz, J=11.5 Hz), 7.57 (d, 2H, J=8.9 Hz), 7.66 (d, 2H, J=8.7 Hz), 9.19 (s, 11H), 9.33 (s, 1H); $^{13}$C NMR (acetone-d$_6$) δ 12.68, 13.38, 19.71, 21.75, 33.42, 34.69, 40.15, 43.92, 119.97, 120.06, 120.57, 120.67, 123.11, 128.50, 129.98, 130.49, 130.79, 136.79, 138.32, 138.41, 139.12, 149.88, 164.80, 165.38; HRMS (ES) calcd for C$_{28}$H$_{35}$ClN$_2$O$_2$ (M+Na) 489.2285, found 489.2266.

Example 46

N-(4'-Bromoacetamidophenyl)retinamide (44)

Synthesis was performed as described for N-(4'-chloroacetamidophenyl)retinamide except using bromoacetyl bromide. The product was purified using column chromatography on silica gel (100% ethyl acetate). $^1$H NMR (acetone-d$_6$) δ 1.04 (s, 6H), 1.47–1.50 (m, 2H), 1.61–1.64 (m, 2H), 1.71 (s, 3H), 2.03–2.09 (m, 5H), 2.42 (d, 3H, J=0.7 Hz), 4.01 (s, 2H), 6.02 (s, 1H), 6.16–6.38 (m, 4H), 7.05 (dd, 1H, J=15.4 Hz, J=11.3 Hz), 7.59 (d, 2H, J=8.8 Hz), 7.69 (d, 2H, J=8.8 Hz), 9.21 (s, 1H), 9.47 (s, 1H); $^{13}$C NMR (acetone-d$_6$) δ 12.72, 13.42, 19.75, 21.79, 33.46, 34.74, 40.19, 120.04, 120.12, 120.39, 120.48, 123.17, 128.54, 130.02, 130.53, 130.83, 134.91, 136.83, 138.36, 138.44, 139.16, 149.92, 164.94, 165.41; HRMS (ES) calcd for C$_{28}$H$_{35}$BrN$_2$O$_2$ (M+Na) 533.1780, found 533.1771.

Characterization of Compounds

Inhibition of Cancer Cell Growth

The ability of the arylretinamides prepared as described in comparative examples A–E and examples 2–46 to inhibit growth of cultured MCF-7 cells was also determined. MCF-7 cells were maintained in DMEM supplemented as recommended by ATCC. Cells were plated (10,000/well) and dosed 24 h later dosed with the arylretinamide. Effects of individual arylretinamides on cell number were assessed 48 hours after a single dose on compound typically administered at a concentration of 10–5M. Activity of the present arylretinamides were compared to vehicle treated cells and cells treated with the arylretinamides of comparative examples A–E. The assay is described in detail in—Jones, P A; Baker, V A; Irwin, A; Earl, L K Toxicol. In Vitro 1997, 11, 769, which is specifically incorporated herein by reference. The results are shown in Tables 1 and 2 below. Those compounds with +or ++activity, and selected others were submitted to the more specific measurement of apoptosis-inducing activity.

Induction of Apoptosis

Figure 4:
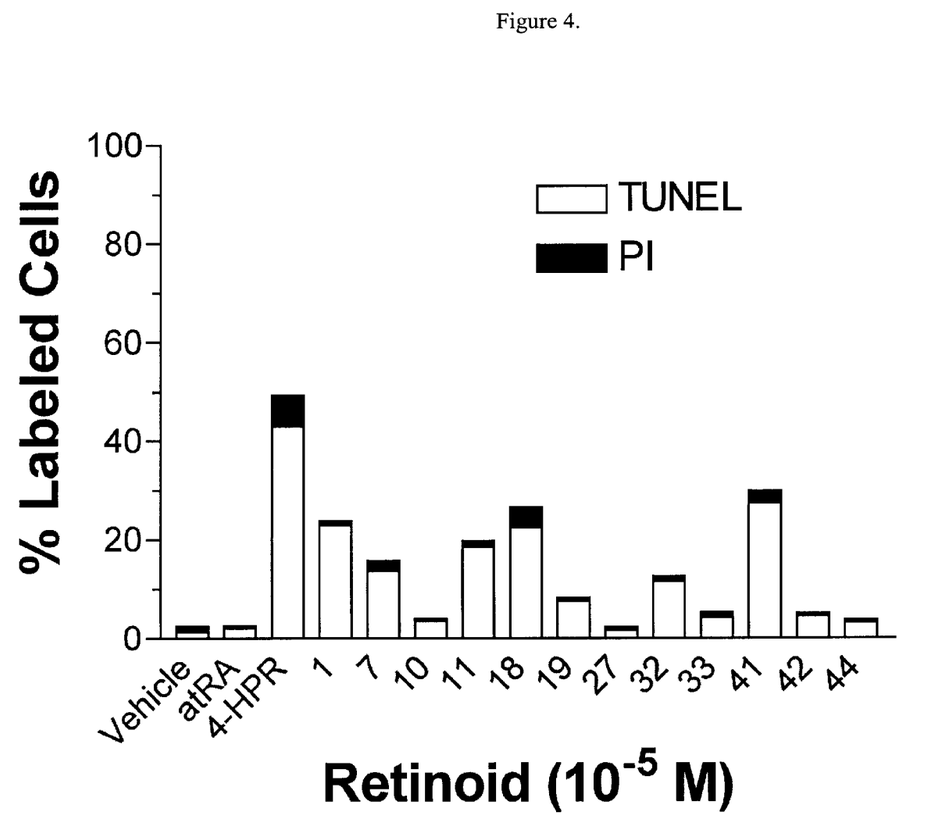
FIG. 4 shows the effect of some of the present arylretinamides on inducing apoptosis of cells in the human breast cancer cell line MCF-7.

The ability of arylretinamides 1, 7, 10, 11, 18, 19, 27, 32, 33, 41, 42, and 44 to induce apoptosis in MCF-7 cells was determined using a TUNEL assay as described in Engeland, M V; Nieland, L J W; Ramackers, F C S; Schutte, B; Reutelingsperger, C P M Cytometry 1998, 31, 1, which is specifically incorporated by reference. As shown in FIG. 4, the new arylretinamides 1, 7, 11, 18, and, perhaps, 32 are effective at inducing apoptosis of the cells in this human breast cancer cell line.

TABLE 1

Anilinamide analogs

| Compound | $R_2$ | $R_3$ | $R_4$ | $R_5$ | $R_6$ | % yield | growth[a] inhibition |
|---|---|---|---|---|---|---|---|
| 1 | $CH_3$ | H | OH | H | H | 71 | − |
| 2 | $CH_3$ | H | OH | $CH_3$ | H | 85 | − |
| 3 | OH | H | $CH_3$ | H | H | 66 | − |
| 4 | OH | H | H | $CH_3$ | H | 80 | − |
| 5 | OH | H | H | $C(CH_3)_3$ | H | 75 | − |
| 6 | OH | H | H | H | $CH_3$ | 83 | − |
| 7 | H | OH | $CH_3$ | H | H | 80 | + |
| 8 | $CH_3$ | OH | H | H | H | 71 | − |
| 9 | H | OH | $OCH_3$ | H | H | 66 | − |
| 10 | Cl | H | OH | H | H | 75 | − |
| 11 | H | Cl | OH | H | H | 70 | + |
| 12 | OH | H | H | Cl | H | 59 | − |
| 13 | H | Cl | OH | Cl | H | 75 | − |
| 14 | H | Br | OH | Br | H | 75 | − |
| 15 | OH | Cl | $CH_3$ | Cl | H | 31 | − |
| 16 | $NO_2$ | H | OH | H | H | 70 | − |
| 17 | H | $NO_2$ | OH | H | H | 74 | − |
| 18 | OH | H | $NO_2$ | H | H | 28 | ++ |
| 19 | OH | H | H | $NO_2$ | H | 20 | ++ |
| 20 | OH | $CO_2CH_3$ | H | H | H | 64 | − |
| 21 | OH | $CO_2H$ | H | H | H | 77 | − |
| 22 | OH | H | $CO_2H$ | H | H | quant. | − |
| 23[c] | OH | H | H | H | $CO_2CH_3$ | 59 | − |
| 24[d] | OH | H | H | H | $CO_2H$ | 36 | − |
| 25[e] | H | OH | $CO_2CH_3$ | H | H | 61 | − |
| 26 | H | OH | $CO_2H$ | H | H | 61 | − |
| 27 | H | $CO_2CH_3$ | OH | H | H | 81 | + |
| 28 | H | $CO_2H$ | OH | H | H | 76 | − |
| 29 | OH | H | H | $CO_2CH_3$ | H | quant. | − |
| 30 | OH | H | $SO_2CH_2CH_3$ | H | H | 75 | − |
| 31 | $CH_2OH$ | H | H | H | H | 57 | ND[f] |
| 32 | H | $CH_2OH$ | H | H | H | 80 | + |
| 33 | H | H | $NH_2$ | H | H | 76 | + |
| 34 | H | H | $NHCOCH_3$ | H | H | 56 | ND |
| 35 | H | H | $NHCOCF_3$ | H | H | 88 | ND |
| 36 | H | H | $N_3$ | H | H | 86 | ND |
| 37 | OH | H | $N_3$ | H | H | 13 | ND |
| 38 | H | H | NCS | H | H | 55 | ND |
| 39 | H | H | $NHCOCH_2Cl$ | H | H | 50 | ND |
| 40 | H | H | $NHCOCH_2Br$ | H | H | 80 | ND |
| 41[b] | H | H | OH | H | H | 94 | ++ |
| 42[b] | OH | H | $CO_2CH_3$ | H | H | 86 | + |
| 43[b] | $CO_2CH_3$ | H | H | H | H | 64 | ND |
| 44[b] | $CO_2H$ | H | H | H | H | 74 | + |
| 45[b,g] | H | H | $OCH_2CH_3$ | H | H | 63 | − |

[a]activity vs. 4-HPR standard, all at $10^{-5}$M: ++ = >50% the activity of standard, + = <50% the activity of standard, − = activity equivalent to vehicle; [b]previously reported comparative example; [c]at 5.9 × $10^{-6}$M; [d]at 3.9 × $10^{-6}$M; [e]at 6.6 × $10^{-6}$M; [f]not determined; [g]at 7.4 × $10^{-6}$M.

TABLE 2

Naphthylamine amide analogs

| Compound | position Ret NH | OH | % yield | growth[a] inhibition |
|---|---|---|---|---|
| 47 | 1 | 2 | 37 | — |
| 48 | 1 | 4 | 26 | — |
| 49 | 1 | 5 | 43 | — |
| 50 | 2 | 3 | 88 | — |

[a]as in Table 1.

46

What is claimed is:

1. A method of preparing an arylretinamide comprising:

a) reacting hexachloroacetone with a solvent-suspended resin-bound triphenylphosphine to provide a suspension comprising an activated chlorinating reagent;

b) reacting retinoic acid with the activated chlorinating reagent to provide retinoyl chloride;

c) adding pyridine and a select arylamine to the reaction mixture and stirring the resulting mixture for a time and at a temperature sufficient for the arylamine to react with the retinoyl chloride and provide the arylretinamide.

2. The method of claim 1 further comprising the step of purifiying the arylretinamide from the suspension.

3. The method of claim 2 wherein purification is accomplished by treatment of the reaction mixture with solid phase reagents to remove unreacted starting materials followed by chromatography.

4. The method of claim 1 wherein step (a) is performed at a temperature ranging from about 0° C. to room temperature.

* * * * *